US007943586B2

(12) United States Patent
Zheng et al.

(10) Patent No.: US 7,943,586 B2
(45) Date of Patent: May 17, 2011

(54) ANTINEOPLASTIC AGENTS TARGETED VIA GLUT TRANSPORTERS

(75) Inventors: Gang Zheng, West Grove, PA (US); Jerry D. Glickson, Ambler, PA (US); Britton Chance, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/560,075

(22) PCT Filed: Jun. 9, 2004

(86) PCT No.: PCT/US2004/018143
§ 371 (c)(1),
(2), (4) Date: Dec. 9, 2005

(87) PCT Pub. No.: WO2004/110255
PCT Pub. Date: Dec. 23, 2004

(65) Prior Publication Data
US 2006/0171893 A1 Aug. 3, 2006

Related U.S. Application Data

(60) Provisional application No. 60/476,648, filed on Jun. 9, 2003, provisional application No. 60/537,282, filed on Jan. 16, 2004, provisional application No. 60/540,700, filed on Jan. 30, 2004, provisional application No. 60/548,240, filed on Feb. 27, 2004.

(51) Int. Cl.
*C07G 3/00* (2006.01)
*C07G 11/00* (2006.01)
*C07H 15/00* (2006.01)
*C07H 17/00* (2006.01)
*C07H 5/06* (2006.01)
*A01N 43/04* (2006.01)
*A61K 31/70* (2006.01)

(52) U.S. Cl. .............. 514/42; 514/24; 514/25; 536/4.1; 536/29.1

(58) Field of Classification Search .................. None
See application file for complete search history.

(56) References Cited

U.S. PATENT DOCUMENTS

| 5,622,936 | A | 4/1997 | Wiessler et al. |
| 6,489,302 | B1 | 12/2002 | Wiessler et al. |
| 6,548,484 | B1 * | 4/2003 | Christian ............... 514/25 |
| 6,989,140 | B2 * | 1/2006 | Tidmarsh et al. ........ 424/9.1 |
| 2002/0198157 | A1 * | 12/2002 | Pandey et al. ........... 514/23 |
| 2003/0181393 | A1 | 9/2003 | Lampidis et al. |
| 2004/0029815 | A1 | 2/2004 | Tidmarsh et al. |
| 2004/0152665 | A1 | 8/2004 | Anastassiades |

FOREIGN PATENT DOCUMENTS

| WO | WO 92/11012 A1 | 7/1992 |
| WO | WO 01/82926 A1 | 11/2001 |
| WO | WO 03/099285 A1 | 12/2003 |
| WO | WO 2004/062614 A2 | 7/2004 |

OTHER PUBLICATIONS

Kozyrev et al. Tetrahedron Letters 1996, vol. 37, No. 36, pp. 6431-6434.*
Dufes et al. Pharmaceutical Research, vol. 17, No. 10, 2000.*
Daishu et al. Journal of Chinese Pharmaceutical Sciences 2001, 10 (4).*
Fukuzumi et al. J. Phys. chem. A 2002, 106, 5105-5113.*
Patani et al. Chem Rev. 1996, 96, 3147-3176.*
Abraha, A., et al., "Inhibition of Tumor Cell Proliferation by Dexamethasone:$^{31}$P NMR Studies of RIF-1 Fibrosarcoma cells Perfused in vitro," *NMR in Biomedicine* 9:173-178, Wiley-Liss, Inc. (1996).
Achilefu, S., et al., "Novel Receptor-Targeted Fluorescent Contrast Agents for in Vivo Tumor Imaging," *Invest. Radiol.* 35:479-485, Lippincott Williams & Wilkins, Inc. (2000).
Achilefu, S., et al., "Synthesis, In Vitro Receptor Binding, and In Vivo Evaluation of Fluorescein and Carbocyanine Peptide-Based Optical Contrast Agents," *J. Med. Chem.* 45:2003-2015, American Chemical Society (May 2002).
Aiken, N.R., et al., "$^{31}$P NMR Spectroscopic Studies of the Effects of Cyclophosphamide on Perfused RIF-1 Tumor Cells," *Magn. Reson. Med.* 31:241-247, Williams & Wilkins (1994).
Alavi, A., and Reivich, M., "Guest Editorial: The Conception of FDG-PET Imaging," *Semin. Nucl. Med.* 32:2-5, W.B. Saunders Company (Jan. 2002).
Baidoo, K. E., Mathews, W., and Wagner, H. N., Fluorescent imaging of deoxyglucose. 8th Intl. Conf: Peace through Mind/Brain Science Hamamatsu, Japan, Feb. 2-4, 2000.
Becker, A., et al., "Receptor-targeted optical imaging of tumors with near-infrared fluorescent ligands," *Nature Biotechnol.* 19:327-331, Nature America, Inc. (2001).
Benaron, D.A., et al., "Enabling Molecular Imaging in the Operating Room: the Palomar™ Real-Time Room-Light Molecular Imaging System," *Molecular Imaging* 2:S194, MIT Press (Jul. 2003).
Berkowitz, B.A. and Ackerman, J.J.H., "Proton Decoupled Fluorine Nuclear Magnetic Resonance Spectroscopy In Situ," *Biophys. J.* 51:681-685, Biophysical Society (1987).
Bhujwalla, Z.M., et al., "Energy Metabolism, pH Changes, and Lactate Production in RIF-1 Tumors Following Intratumoral Injection of Glucose," *Int. J. Radiat. Oncol. Biol. Phys.* 22:95-101, Pergamon Press (1991).
Bhujwalla, Z.M., et al., "Glucose Metabolism in RIF-1 Tumors after Reduction in Blood Flow: An In Vivo $^{13}$C and $^{31}$P NMR Study," *Magn. Reson. Med.* 32:303-309, Williams & Wilkins (1994).

(Continued)

*Primary Examiner* — Layla Bland
(74) *Attorney, Agent, or Firm* — Sterne, Kessler, Goldstein & Fox P.L.L.C.

(57) ABSTRACT

The present invention relates to novel antineoplastic agents and cancer diagnostic agents that specifically target neo-plastic cells via the GLUT transportation system. More specifically, the invention relates to conjugates of 2-deoxyglucose, wherein a linker, which includes a covalent bond, is attached to 2-deoxyglucose at the 2 position, and the linker is attached to a therapeutic or diagnostic agent. The invention also relates to methods of treating tumor disease and methods of making the novel compounds of the present invention. The agents of the present invention are superior to previous agents as they are targeted via GLUT transporters.

3 Claims, 15 Drawing Sheets

OTHER PUBLICATIONS

Binder C. et al., "Deregulated Simultaneous Expression of Multiple Glucose Transporter Isoforms in Malignant Cells and Tissues," *Anticancer Res.* 17:4299-4304, J.G. Delinassios (1997).

Blokland, J.A., et al., "Positron emission tomography: a technical introduction for clinicians," *Eur. J. Radiol.* 44:70-75, Elsevier Science Ireland Ltd. (Oct. 2002).

Braunschweiger, P.G., et al., "Potentiation of Interleukin 1 α Mediated Antitumor Effects by Ketoconazole," *Cancer Res.* 50:4709-4717, American Association for Cancer Research (1990).

Briasoulis, E., et al., "Phase I Trial of 6-Hour Infusion of Glufosfamide, a New Alkylating Agent With Potentially Enhanced Selectivity for Tumors That Overexpress Transmembrane Glucose Transporters: A Study of the European Organization for Research and Treatment of Cancer Early Clinical Studies Group," *J. Clin. Oncol.* 18:3535-3544, American Society of Clinical Oncology (2000).

Bugaj, J.E., et al., "Novel fluorescent contrast agents for optical imaging of in vivo tumors based on a receptor-targeted dye-peptide conjugate platform," *J. Biomed. Opt.* 6:122-133, SPIE (2001).

Chance, B., et al., "Oxidation-Reduction Ratio Studies of Mitochondria in Freeze-trapped Samples," *J. Biol. Chem.* 254:4764-4771, American Society for Biochemistry and Molecular Biology (1979).

Chance, B., et al., "Highly sensitive object location in tissue models with linear in-phase and anti-phase multi-element optical arrays in one and two dimensions," *Proc. Natl. Acad. Sci. USA* 90:3423-3427, National Academy of Sciences (1993).

Chance, B., et al., "Precision localization of hidden absorbers in body tissues with phased-array optical systems," *Rev. Sci. Instrum.* 67:4324-4332, American Institute of Physics (1996).

Chang, C.H.F., et al., "The Interactions of Gallium with Various Buffers and Chelating Agents in Aqueous Solution: Gallium-71 and Hydrogen-1 NMR Sstudies," *Bioinorg. Chem.* 8:11-19, Elsevier North-Holland, Inc. (1978).

Chen, Y., et al., "Bacteriopurpurinimides: Highly Stable and Potent Photosensitizers for Photodynamic Therapy," *J. Med. Chem.* 45:255-258, American Chemical Society (Jan. 2002).

Chen, Y., et al., "Near-infrared phase cancellation instrument for fast and accurate localization of fluorescent heterogeneity," *Rev. Sci. Instrum.* 74:3466-3473, American Institute of Physics (Jul. 2003).

Chen, Y., et al., "Metabolism-enhanced tumor localization by fluorescence imaging: in vivo animal studies," *Optics Lett.* 28:2070-2072, Optical Society of America (Nov. 2003).

Cohade, C., and Wahl, R.L., "PET Scanning and Measuring the Impact of Treatment," *Cancer J.* 8:119-134, Jones and Bartlett Publishers, Inc. (Mar./Apr. 2002).

Colvin, M. and Hilton, J., "Pharmacology of Cyclophosphamid and Metabolites," *Cancer Treat. Rep.* 65:89-95, U.S. National Cancer Institute (1981).

Colvin, M., "The Comparative Pharmacology of Cyclophosphamide and Ifosphamide," *Semin. Oncol.* 9:2-7, Grune & Stratton, Inc. (1981).

Colvin, O.M., "An Overview of Cyclophosphamide Development and Clinical Applications," *Curr. Pharm. Design* 5:555-560, Bentham Science Publishers B.V. (1999).

Colvin, O.M., et al.,"Role of Glutathione in Cellular Resistance to Alkylating Agents," *Adv. Enzyme Regul.* 33:19-26, Pergamon Press Ltd. (1993).

Czernin, J., "Clinical Applications of FDG-PET in Oncology," *Acta Medica Austriaca* 29:162-170, Blackwell Publishing Ltd. (Nov. 2002).

Czemin, J. and Phelps, M.E., "Positron Emission Tomography Scanning: Current and Future Applications," *Ann. Rev. Med.* 53:89-112, Annual Reviews (Feb. 2002).

Deuel, R.K., et al., "Monitoring the Time Course of Cerebral Deoxyglucose Metabolism by $^{31}P$ Nuclear Magnetic Resonance Spectroscopy," *Science* 228:1329-1331, American Association for the Advancement of Science (1985).

Dougherty, T.J., et al., "Photodynamic Therapy," *J. Natl. Cancer Inst.* 90:889-905, Oxford University Press (1998).

Duvvuri, U., et al., "Quantitative $T_{1p}$ magnetic Resonance Imaging of RIF-1 Tumors in Vivo: Detection of Early Response to Cyclophosphamide Therapy," *Cancer Res.* 61:7747-7753, American Association for Cancer Research (2001).

Fiedor, J., et al., "Photodynamics of the Bacteriochlorophyll-Carotenoid System. 2. Influence of Central Metal, Solvent and β-Carotene on Photobleaching of Bacteriochlorophyll Derivatives," *Photochem. Photobiol.* 76:145-152, American Society for Photobiology (Aug. 2002).

Fishkin, J.B., and Gratton, E., "Propagation of photon-density waves in strongly scattering media containing an absorbing semi-infinite plane bounded by a straight edge," *J. Opt. Soc. Am.* 10:127-140, Optical Society of America (1993).

Flanagan, Jr., J.H., et al., "Functionalized Tricarbocyanine Dyes as Near-Infrared Fluorescent Probes for Biomolecules," *Bioconj. Chem.* 8:751-756, American Chemical Society (1997).

Flier, J.S., et al., "Elevated Levels of Glucose Transport and Transporter Messenger RNA are Induced by *ras* or *src* Oncogenes," *Science* 235:1492-1495, American Association for the Advancement of Science (1987).

Folli, S., et al., "Antibody-Indocyanin Conjugates for Immunophotodetection of Human Squamous Cell Carcinoma in Nude Mice," *Cancer Res.* 54:2643-2649, American Association for Cancer Research (1994).

Friedman, H.S., et al., "Glutathione Protects Cardiac and Skeletal Muscle from Cyclophosphamide-induced Toxicity," *Cancer Res.* 50:2455-2462, American Association for Cancer Research (1990).

Friedman, H.S., et al., "$O^6$-Benzylguanine-mediated Enhancement of Chemotherapy," *Mol. Cancer Thera.* 1:943-948, American Association for Cancer Research, Inc. (Sep. 2002).

Fung, L.K., et al., "Pharmacokinetics of Interstitial Delivery of Carmustine, 4-Hydroperoxycyclophosphamide, and Paclitaxel from a Biodegradable Polymer Implant in the Monkey Brain," *Cancer Res.* 58:672-684, American Association for Cancer Research (1998).

Gambhir, S.S., "Molecular Imaging of Cancer with Positron Emission Tomography," *Nature Rev. Cancer* 2:683-693, Nature Publishing Group (Sep. 2002).

Gams, R.A., et al., "Serum Inhibition of in Vitro $^{67}Ga$ Binding by L1210 Leukemic Cells," *Cancer Res.* 35:1422-1426, American Association for Cancer Research (1975).

Gams, R.A., et al., "Effect of Growth Rate and Simian Adenovirus-7 Transformation on in vitro $^{67}Ga$ Binding to Hamster Embryo Cells," *J. Nucl. Med.* 16:231-233, Society of Nuclear Medicine (1975).

Giorgetti, A., et al., "Clinical oncological Applications of Positron Emission Tomography (PET) using Fluorine-18-Fluoro-2-deoxy-D-glucose," *Radiol. Med.* 103:293-318, Springer Milan (Apr. 2002).

Glickson, J.D., et al., "In Vitro Binding of $^{67}Ga$ to L1210 cells," *Cancer Res.* 33:2706-2713, American Association for Cancer Research (1973).

Gu, Y.Q., et al., "High-resolution three-dimensional scanning optical image system for intrinsic and extrinsic contrast agents in tissue," *Rev. Sci. Instrum.* 73:172-178, American Institute of Physics (Jan. 2002).

Gurfinkel, M., et al., "Pharmacokinetics of ICG and HPPH-car for the Detection of Normal and Tumor Tissue using Fluorescense, Near-infrared Reflectance Imaging: A Case Study," *Photochem. Photobiol.* 72:94-102, American Society for Photobiology (2000).

Hamburger, A.W., and Salmon, S.E., "Primary Bioassay of Human Tumor Stem Cells," *Science* 197:461-463, American Association for the Advancement of Science (1977).

Harris, D.S., et al., "Polarized distribution of glucose transporter isoforms in Caco-2 cells," *Proc. Natl. Acad. Sci. USA* 89:7556-7560, National Academy of Sciences (1992).

Hartwich, G., et al., "Metal-Substituted Bacteriochlorophylls. 1. Preparation and Influence of Metal and Coordination on Spectra," *J. Am. Chem. Soc.* 120:3675-3683, American Chemical Society (1998).

Helliwell, P.A., and Kellett, G.L., "The active and passive components of glucose absorption in rat jejunum under low and high perfusion stress," *J. Physiol.* 544:579-589, The Physiological Society (Oct. 2002).

Henderson, B.W., et al., "An in Vivo Quantitative Structure-Activity Relationship for a Congeneric Series of Pyropheophorbide Derivatives as Photosensitizers for Photodynamic Therapy," *Cancer Res.* 57:4000-4007, American Association for Cancer Research (1997).

Hustinx, R., et al., Whole-Body FDG-PET Imaging in the Management of Patients With Cancer, *Semin. Nucl. Med.* 32:35-46, W.B. Saunders Company (Jan. 2002).

Inoue, T., et al., "A shifting landscape: What will be next FDG in PET oncology?" *Ann. Nucl. Med.* 16:1-9, Japanese Society of Nuclear Medicine (Feb. 2002).

Intes, X., et al., "Detection limit enhancement of fluorescent heterogeneities in turbid media by dual-interfering excitation," *Appl. Opt.* 41:3999-4007, Optical Society of America (Jul. 2002).

Ishikawa N, et al., "*SGLT* Gene Expression in Primary Lung Cancers and Their Metastatic Lesions," *Jpn. J. Cancer Res.* 92:874-879, Japanese Cancer Association (2001).

Jahde, E., et al., "Hydrogen Ion-Mediated Enhancement of Cytotoxicity of Bis-Chloroethylating Drugs in Rat Mammary Carcinoma Cells in Vitro," *Cancer Res.* 49:2965-2972, American Association for Cancer Research (1989).

Jahde, E., et al., "pH in Human Tumor Xenografts and Transplanted Rat Tumors: Effect of Insulin, Inorganic Phosphate, and *m*-Iodobenzylguanidine," *Cancer Res.* 52:6209-6215, American Association for Cancer Research (1992).

Jerusalem, G., et al., "The value of positron emission tomography (PET) imaging in disease staging and therapy assessment," *Ann. Oncol.* 13:227-234, European Society for Medical Oncology (Oct. 2002).

Kaizer, H., et al., "Autologous Bone Marrow Transplantation in Acute Leukemia and Non-Hodgkin's Lymphoma: A Phase I Study of 4-Hydroperoxycyclophosphamide (4HC) Incubation of Marrow Prior to Cryopreservation," *Haematol. Blood Transfus.* 28:90-101, Springer-Verlag (1983).

Kaplan, O., et al., "Effects of 2-Deoxyglucose on Drug-sensitive and Drug-Resistant Human Breast Cancer Cells: Toxicity and Magnetic Resonance Spectroscopy Studies of Metabolism," *Cancer Res.* 3:544-551, American Association for Cancer Research (1990).

Kotyk, J.J., et al., "Simultaneous In Vivo Monitoring of Cerebral Deoxyglucose and Deoxyglucose-6-Phosphate by $^{13}C\{1H\}$ Nuclear Magnetic Resonances Spectroscopy," *J. Neurochem.* 53:1620-1628, Raven Press, Ltd. (1989).

Kozyrev, A.N., et al., "Syntheses of Stable Bacteriochlorophyll-a Derivatives as Potential Photosensitizers for Photodynamic Therapy," *Tetrahedron Lett.* 37:6431-6434, Elsevier Science Ltd. (1996).

Kuin, A., et al., "Reduction of Intratumoral pH by the Mitochondrial Inhibitor *m*-Iodobenzylguanidine and Moderate Hyperglycemia," *Cancer Res.* 54:3785-3792, American Association for Cancer Research (1994).

Kuin, A., et al., "Potentiation of anti-cancer dug activity at low intratumoral pH induced by the mitochondrial inhibitor *m*-iodobenzylguanidine (MIBG) and its analogue benzylguanidine (BG)," *Br. J. Cancer* 79:793-801, Nature Publishing Group (1999).

Leppens-Luisier, G., et al., "Facilitated glucose transporters play a crucial role throughout mouse preimplantation embryo development," *Hum. Reprod.* 16:1229-1236, European Society of Human Reproduction and Embryology (2001).

Li, H., et al., NIR Optical Probes Targeting Glucose Transporters, SPIE Photonic West Meeting, Jan. 27, 2004.

Li, S.-J., et al., Response of Radiation-induced Fibrosarcoma-1 in Mice to Cyclophosphamide Monitored by in Vivo $^{31}P$ Nuclear Magnetic Resonance Spectroscopy, *Cancer Res.* 48:4736-4742, American Association for Cancer Research (1988).

Licha, K., "Contrast Agents for Optical Imaging," *Top. Curr. Chem.* 222:1-29, Springer-Verlag (Sep. 2002).

Liu, H., et al., "Hypersensitization of Tumor Cells to Glycolytic Inhibitors," *Biochemistry* 40:5542-5547, American Chemical Society (2001).

Liu, H., et al., "Hypoxia increases tumor cell sensitivity to glycolytic inhibitors: a strategy for solid tumor therapy (Model C)," *Biochem. Pharmacol.* 64:1746-1751, Elsevier Science Inc. (Dec. 2002).

Lin, Y., et al., "Novel Near-Infrared Cyanine Fluorochromes: Synthesis, Properties, and Bioconjugation," *Bioconjugate Chem.* 13:605-610, American Chemical Society (May-Jun. 2002).

Lloyd, P.G., et al., "Examining Glucose Transport in Single Vascular Smooth Muscle Cells with a Fluorescent Glucose Analog," *Physiol. Res.* 48:401-410, The Institute of Physiology of The Czechoslovak Academy of Sciences (1999).

Ludeman, S.M., "The Chemistry of the Metabolites of Cyclophosphamide," *Curr. Pharm. Design* 5:627-643, Bentham Science Publishers B.V. (1999).

Maisey, M.N., "Overview of clinical PET," *Br. J. Radiol.* 75:S1-S5, British Institute of Radiology (Nov. 2002).

Maschek, G., et al., "2-Deoxy-D-glucose Increases the Efficacy of Adriamycin and Paclitaxel in Human Osteosarcoma and Non-Small Cell Lung Cancers in Vivo," *Cancer Res.* 64:31-34, American Association for Cancer Research (Jan. 2004).

Medina, R.A. and Owen, G.I., "Glucose transporters: expression, regulation and cancer," *Biol. Res.* 35:9-26, Society of Biology of Chile (Apr. 2002).

Moon, W.K., et al., "Enhanced Tumor Detection Using a Folate Receptor-Targeted Near-Infrared Fluorochrome Conjugate," *Bioconjug. Chem.* 14:539-545, American Chemical Society (May-Jun. 2003).

Moreb, J., et al., "Role of Sldehyde Dehydrogenase in the Protection of Hematopoietic Progenitor Cells from 4-Hydroperoxycyclophosphamide by interleukin 1 β and Tumor Necrosis Factor," *Cancer Res.* 52:1770-1774, American Association for Cancer Research (1992).

Mujumdar, S.R., et al., "Cyanine-Labeling Reagents: Sulfobenzindocyanine Succinimidyl Esters," *Bioconjugate Chem.* 7:356-362, American Chemical Society (1996).

Natarajan, A., and Srienc, F., "Glucose uptake rates of single *E. coli* cells grown in glucose-limited chemostat cultures," *J. Microbiol. Methods* 42:87-96, Elsevier Science B.V. (2000).

Oh, K.-B. and Matsuoka, H., "Rapid viability assessment of yeast cells using vital staining with 2-NBDG, a fluorescent derivative of glucose," *Int. J. Food Microbiol.* 76:47-53, Elsevier Science B.V. (Jun. 2002).

Pandey, R.K. and Zheng, G., "Porphyrins as Photosensitizers in Photodynamic Therapy," in *The Porphyrins handbook*, Kadish, K.M., et al., eds., Academic Press, Boston, MA, pp. 157-230 (2000).

Park, K.-H., et al., "Probe of specific interaction between a simplified synthetic glycopolymer and erythrocytes as mediated by a glucose transporter (GLUT) on a cell membrane," *J. Biomed. Mater. Res.* 59:591-594, John Wiley & Sons, Inc. (Mar. 2002).

Patterson, M.S., et al., "Time resolved reflectance and transmittance for the non-invasive measurement of tissue optical properties," *Appl. Opt.* 28:2331-2336, Optical Society of America (1989).

Pauwels, E.K.J., et al., "FDG Accumulation and Tumor Biology," *Nucl. Med. Biol.* 25:317-322, Elsevier Science Inc. (1998).

Quistorff, B., et al., "High Spatial Resolution Readout 3-D /metabolic Organ Structure: An Aautomated, Low-Temperature Redox Ratio-Scanning Instrument," *Anal. Biochem.* 148:389-400, Academic Press (1985).

Rajan, S.S., et al., "$^{31}P$ NMR Spectroscopic Study of Bioenergetic Changes in Radiation-induced Fibrosarcoma-1 After Radiation Therapy," *NMR in Biomedicine* 2:165-171, Hayden & Son Limited (1989).

Ramanujam, N., et al., "Low temperature fluorescence imaging of freeze-trapped human cervical tissues," *Opt. Express* 8:335-343, Optical Society of America (2001).

Román, Y., et al., "Confocal microscopy study of the different patterns of 2-NBDG uptake in rabbit enterocytes in the apical and basal zone," *Pflügers Arch.-Eur. J. Physiol.* 443:234-239, Springer-Verlag (2001).

Rosenbach-Belkin, V., et al., "Serine Conjugates of Chlorophyll and Bacteriochlorophyll: Photocytotoxicity in vitro and Tissue Distribution in Mice Bearing Melanoma Tumors," *Photochem. Photobiol.* 64:174-181, American Society for Photobiology (1996).

Russo, J.E., et al., "The Role of Aldehyde Dehydrogenase Isozymes in Cellular Resistance to the Alkylating Agent Cyclophosphamide," *Enzymol. Mol. Biol. Carbonyl. Metabol.* 2:65-79, Alan R. Liss, Inc. (1989).

Schiffer, L.M., and Braunschweiger, P.G., "Preliminary Observations on the Correlation of Proliferative Phenomena with in Vivo $^{31}$P NMR Spectroscopy after Tumor Chemotherapy," *Ann. N.Y. Acad. Sci.* 459:270-277, New York Academy of Sciences (1985).

Schreiber, S., et al., "Local Photodynamic Therapy (PDT) of Rat C6 Glioma Xenografts with Pd-Bacteriopheophorbide Leads to Decreased Metastases and Increase of Animal Cure Compared with Surgery," *Int. J. Cancer* 99:279-285, Wiley-Liss, Inc. (May 2002).

Schwaiger, M., "Functional imaging for assessment of therapy," *Br. J. Radiol.* 75:S67-S73, British Institute of Radiology (Nov. 2002).

Semenza, G.L., and Wang, G.L., "A Nuclear Factor Induced by Hypoxia via De Novo Protein Synthesis Binds to the Human Erythropoietin Gene Enhancer at a Site Required for Transcriptional Activation," *Mol. Cell. Biol.* 12:5447-5454, American Society for Microbiology (1992).

Speizer, L., et al., "Asymmetric transport of a fluorescent glucose analogue by human erythrocytes," *Biochim. Biophys. Acta* 815:75-84, Elsevier Science Publishers B.V. (1985).

Sternberg, E.D., and Dolphin, D., "Porphyrin-based Photosensitizers for Use in Photodynamic Therapy," *Tetrahedron* 54:4151-4202, Elsevier Science Ltd. (1998).

Stüben, J., et al., "Pharmacokinetics and whole-body distribution of the new chemotherapeutic agent β-D-glucosylisophosphoramide mustard and its effects on the incorporation of [methyl-3H]-thymidine in various tissues of the rat," *Cancer Chemother. Pharmacol.* 38:355-365, Springer-Verlag (1996).

Teerijoki, H., et al., "Monosaccharide uptake in common carp (*Cyprinus carpio*) EPC cells is mediated by a facilitative glucose carrier," *Comp. Biochem. Physiol. Part B* 128:483-491, Elsevier Science Inc. (2001).

Turkington, T.G. and Coleman, R.E., "Clinical Oncologic Positron Emission Tomography: An Introduction," *Seminars in Roentgenology* 37:102-109, Elsevier Science (Apr. 2002).

Twentyman, P.R., et al., "A New Mouse Tumor System (RIF-1) for Comparison of End-Point Studies," *J. Natl. Cancer Inst.* 49:595-604, Oxford University Press (1980).

Van De Wiele, C., et al., "Nuclear Medicine Imaging to Predict Response to Radiotherapy: A Review," *Int. J. Rad. Oncol. Biol. Phys.* 55:5-15, Elsevier Science Inc. (Jan. 2003).

Vaupel, P., et al., "Blood Flow, Oxygen and Nutrient Supply, and Metabolic Microenvironment of Human Tumors: A Review," *Cancer Res.* 49:6449-6465, American Association for Cancer Research (1989).

Veyhl, M., et al., "Transport of the new chemotherapeutic agent β-D-glucosylisophosphoramide mustard (D-19575) into tumor cells is mediated by the Na$^+$-D-glucose cotransporter SAAT1," *Proc. Natl. Acad. Sci. USA* 95:2914-2919, National Academy of Sciences (1998).

Warburg, Otto (Ed.), "*The Metabolism of Tumours*," Constable & Co., Ltd., London (1930).

Wehrle, J.P., et al., "$^{31}$P and $^1$H NMR Spectroscopy of Tumors in Vivo: Untreated Growth and Response to Chemotherapy," *Ann. N.Y. Acad. Sci.* 508:200-215, New York Academy of Sciences (1987).

Weinhouse, S., "The Warburg Hypothesis Fifty Years Later," *Cancer Res. Clin. Oncol.* 87:115-126, Springer-Verlag (1976).

Weishaupt, K.R., et al., "Identification of Singlet Oxygen as the Cytotoxic Agent in Photo-Inactivation of a Murine Tumor," *Cancer Res.* 36:2326-2329, American Association for Cancer Research (1976).

Weissleder, R., et al., "In vivo imaging of tumors with protease-activated near-infrared fluorescent probes," *Nature Biotechnol.* 17:375-378, Nature America Inc. (1999).

Weissleder, R., and Mahmood, U., "Molecular Imaging," *Radiology* 219:316-333, Radiological Society of North America (2001).

Weissleder, R., and Ntziachristos, V., "Shedding light onto live molecular targets," *Nature Med.* 9:123-128, Nature Publishing Company (Jan. 2003).

Wood, I.S., and Trayhurn, P., "Glucose transporters (GLUT and SGLT): expanded families of sugar transport proteins," *Br. J. Nutr.* 89:3-9, CABI Publishing (2003).

Yamada, K., et al., "Measurement of Glucose Uptake and Intracellular Calcium Concentration in Single, Living Pancreatic β-cells," *J. Biol. Chem.* 275:22278-22283, American Society for Biochemistry and Molecular Biology (2000).

Yamamoto, T., et al., "Over-Expression of Facilitative Glucose Transporter Genes in Human Cancer," *Biochem. Biophys. Res. Commun.* 170, 223-230, Academic Press (1990).

Yoshioka, K., et al., "Intracellular Fate of 2-NBDG, a Fluorescent Probe for Glucose Uptake Activity, in *Escherichia coli* cells," *Biosci. Biotech. Biochem.* 60:1899-1901, Japan Society for Bioscience, Biotechnology, and Agrochemistry (1996).

Yoshioka, K., et al., "A novel fluorescent derivative of glucose applicable to the assessment of glucose uptake activity of *Escherichia coli*," *Biochim. Biophys. Acta* 1289:5-9, Elsevier Science B.V. (1996).

Zhang, M., et al., "Pyropheophorbide 2-Deoxyglucosamide: A New Photosensitizer Targeting Glucose Transporters," *Bioconj. Chem.* 14:709-714, American Chemical Society (Jul./Aug. 2003).

Zhang, Z., et al., "Redox ratio of mitochondria as an indicator for the response of photodynamic therapy," *J. Biomed. Optics* 9:772-778, SPIE (Jul./Aug. 2004).

Zhang, Z., et al., "Metabolic Imaging of Tumors using Intrinsic and Extrinsic Fluorescent Markers," *Biosensors Bioelectronics*, 20: 643-50 (2004).

Zheng, G., et al., "Synthesis, Photophysical Properties, Tumor Uptake, and Preliminary in Vivo Photosensitizing Efficacy of a Homologous Series of 3-(1'-Alkyloxy) Ethyl-3-devinaylpurpurin-18-*N*-alkylimides with Variable Lipophilicity," *J. Med. Chem.* 44:1540-1559, American Chemical Society (2001).

Zheng, G., et al., "Contrast-enhanced near-infrared (NIR) Optical Imaging for Subsurface Cancer Detection," *J. Porphyrins Phtalocyanines*, 8:1106-17 (2004).

Zheng, G., et al., "Tricarbocyanine Cholesteryl Laurates Labeled LDL: New Near Infrared Fluorescent Probes (NIRFs) for Monitoring Tumors and Gene Therapy of Familial Hypercholesterolemia," *Bioorg. Med. Chem. Lett.* 12:1485-1488, Elsevier Science Ltd. (Jun. 2002).

Zheng, G., et al., "Low-Density Lipoprotein Reconstituted by Pyropheophorbide Cholesteryl Oleate as Target-Specific Photosensitizer," *Bioconj. Chem.* 13:392-396, American Chemical Society (May-Jun. 2002).

Zheng, G., et al., "Contrast-enhanced near-infrared (NIR) optical imaging for subsurface cancer detection," *J. Porphyrins Phtalocyanines* 8:1106-1117, Society of Porphyrins & Phtalocyanines (2004).

Zhou, R., et al., "Enhancement of Hyperglycemia-induced Acidification of human Melanoma Xenografts by Inhibitors of Respiration and Ion Transport," *Acad. Radiol.* 8:571-582, Association of University Radiologists (2001).

Zhou, R., et al., "Intracellular Acidification of Human Melanoma Xenografts by the Respiratory Inhibitor *m*-Iodobenzylguanidine Plus Hyperglycemia: A $^{31}$P Magnetic Resonance Spectroscopy Study," *Cancer Res.* 60:3532-3536, American Association for Cancer Research (2000).

Zon, G., et al., "NMR Spectroscopic Studies of Intermediary Metabolites of Cyclophosphamide. A Comprehensive Kinetic Analysis of the Interconversion of *cis*- and *trans*-4-Hydroxycyclophosphamide with Aldophosphamide and the Concomitant Partitioning of Aldophosphamide Between Irreversible Fragmentation and Reversible Conjugation Pathways," *J. Med. Chem.* 27:466-485, American Chemical Society (1984).

\* cited by examiner

US 7,943,586 B2

ANTINEOPLASTIC AGENTS TARGETED VIA GLUT TRANSPORTERS

STATEMENT REGARDING FEDERALLY-SPONSORED RESEARCH AND DEVELOPMENT

The U.S. Government has a paid-up license in this invention and the right in limited circumstances to require the patent owner to license others on reasonable terms as provided for by the terms of Grant Nos. R21 CA95330 (GZ), N01-CO37119 (GZ), NO1-CM97065 (13C), P20 CA86255 (JDG), R24 CA83105 (JDG) and RO1 CA85831 (TMB) awarded by NIH.

BACKGROUND OF THE INVENTION

1. Field of the Invention

The invention is in the field of antineoplastic agents and cancer diagnostic agents. More particularly, the invention pertains to novel 2-deoxyglucose conjugates, their use and methods of making such compounds.

2. Related Art

One of the biochemical "hallmarks" of malignancy is enhanced tumor glycolysis, which is primarily due to the overexpression of glucose transporters (GLUTs) and the increased activity of mitochondria-bound hexokinase in tumors (Medina, R. A. and Owen, G. I. (2002) Glucose transporters: expression, regulation and cancer. *Biol. Res.* 35, 9-26). Utilizing these cancer signatures, [$^{18}$F] 2-fluoro-2-deoxyglucose ($^{18}$FDG) based positron emission tomography (ET) has become a widely used molecular imaging modality in the detection of a wide range of human cancers (Czemin, J. and Phelps, M. E. (2002) Positron emission tomography scanning: current and future applications. *Ann. Rev. Med.* 53, 89-112).

$^{18}$FDG is an analog of glucose that enters cells via glucose transporters (GLUT) and is phosphorylated to $^{18}$FDG-6-phosphate by hexokinase, the first enzyme in the glycolytic pathway. This enzyme converts glucose, 2-deoxyglucose or $^{18}$FDG from a neutral, membrane-permeable form to an anionic, membrane-impermeable form. Reversal of this reaction requires glucose-6-phosphatase, which is generally not present at high enough concentration in most cells to mediate this reaction. Further metabolism of $^{18}$FDG-6-phosphate by phosphoglucose isomerase, the next enzyme in the glycolytic pathway, or by enzymes in the glycogen or pentose shunt pathways does not occur (Pauwels, E. K., Ribeiro, M. J., Stoot, J. H., McCready, V. R., Bourguignon, M., and Maziere, B. (1998) FDG accumulation and tumor biology. *Nuclear Med. Biol.* 25, 317-322). Therefore, $^{18}$FDG-6-phosphate is trapped in the cell. The high affinity of $^{18}$FDG for tumors derives from the high levels of aerobic glycolysis (Vaupel, P., Kallinowski, F., and Okunieff, P. (1989) Blood flow, oxygen and nutrient supply, and metabolic microenvironment of human tumors: a review. *Cancer Res.* 49, 6449-6465) and overexpression of GLUTs exhibited by most, but not all (Weinhouse, S. (1976) The Warburg hypothesis fifty years later. Z. fur Krebsforsch. *Klin. Onkol.* 87, 115-126), tumors.

Speizer in 1985 (Speizer, L., Haugland, R., and Kutchai, H. (1985) Asymmetric transport of a fluorescent glucose analogue by human erythrocytes. *Biochim. Biophys. Acta* 815, 75-84), exploited the glucose transport pathway to deliver a fluorescent analog of glucose, 6-deoxy-N-(7-nitrobenz-2-oxa-1,3-diazol-4-yl)-aminoglucose, into human erythrocytes. This analog is a derivative of 6-deoxyglucose containing a fluorophore on the 6-position. A fluorescent derivative of 2-deoxyglucose, 2-[N-(7-nitrobenz-2-oxa-1,3-diazol-4-yl)amino]-2-deoxy-D-glucose (2-NBDG) (Ex: 475 nm; Em: 550 nm), was introduced by Yoshioka et al. in 1996 (Yoshioka, K., Takahashi, H., Homma, T., Saito, M., Oh, K. B., Nemoto, Y., and Matsuoka, H. (1996) A novel fluorescent derivative of glucose applicable to the assessment of glucose uptake activity of *Escherichia coli*. *Biochim. Biophys. Acta* 1289, 5-9), who demonstrated that localization of this agent in the yeast Candida albicans was inhibited by D-glucose, but not L-glucose. Similar D-glucose (but not L-glucose) inhibited uptake of 2-NBDG has been demonstrated in *E. coli* (Yoshioka, K., Takahashi, H., Homma, T., Saito, M., Oh, K. B., Nemoto, Y., and Matsuoka, H. (1996) A novel fluorescent derivative of glucose applicable to the assessment of glucose uptake activity of *Escherichia coli*. *Biochim. Biophys. Acta* 1289, 5-9; Yoshioka, K., Saito, M., Oh, K. B., Nemoto, Y., Matsuoka, H., Natsume, M., and Abe, H. (1996) Intracellular fate of 2-NBDG, a fluorescent probe for glucose uptake activity, in *Escherichia coli* cells. *Biosci. Biotech. Biochem.* 60, 1899-1901; and Natarajan, A. and Srienc, F. (2000) Glucose uptake rates of single *E. coli* cells grown in glucose-limited chemostat cultures. *J. Microbiol. Methods,* 42, 87-96), yeast (Natarajan, A. and Srienc, F. (2000) Glucose uptake rates of single *E. coli* cells grown in glucose-limited chemostat cultures. *J. Microbiol. Methods,* 42, 87-96), vascular smooth muscle cells (Oh, K. B. and Matsuoka, H. (2002) Rapid viability assessment of yeast cells using vital staining with 2-NBDG, a fluorescent derivative of glucose. *Intl. J. Food Microbiol.* 76, 47-53), and pancreatic β-cells transfected to overexpress Glut2 glucose transporters (Lloyd, P. G., Hardin, C. D., and Sturek, M. (1999) Examining glucose transport in single vascular smooth muscle cells with a fluorescent glucose analog. *Physiol. Res.* 48, 401-410).

Utilization of the glucose transport system was further supported by competitive inhibition of 2-NBDG uptake by the glucose analogs 3-O-methyl glucose and D-glucosamine (Yoshioka, K., Saito, M., Oh, K. B., Nemoto, Y., Matsuoka, H., Natsume, M., and Abe, H. (1996) Intracellular fate of 2-NBDG, a fluorescent probe for glucose uptake activity, in *Escherichia coli* cells. *Biosci. Biotech. Biochem.* 60, 1899-1901). Internalization of 2-NBDG in isolated rabbit enterocytes was demonstrated by confocal microscopy (Roman, Y., Alfonso, A., Louzao, M. C., Vieytes, M. R., and Botana, L. M. (2001) Confocal microscopy study of the different patterns of 2-NBDG uptake in rabbit enterocytes in the apical and basal zone. *Pflugers Arch.—Eur. J. Physiol.* 443, 234-239). Conversion of 2-NBDG to 2-NBDG-6-phosphate in *E. coli* cells was confirmed by mass spectrometry and by demonstration that glucose-6-phosphatase regenerated 2-NBDG (Yoshioka, K., Saito, M., Oh, K. B., Nemoto, Y., Matsuoka, H., Natsume, M., and Abe, H. (1996) Intracellular fate of 2-NBDG, a fluorescent probe for glucose uptake activity, in *Escherichia coli* cells. *Biosci. Biotech. Biochem.* 60, 1899-1901). Localization of 2-NBDG in rat 9L glioma has recently been reported by Baidoo et al. (13aidoo, K. E., Mathews, W., and Wagner, H. N. (2000) Fluorescent imaging of deoxyglucose. 8*th Intl. Conf: Peace through Mind/Brain Science* Hamamatsu, Japan, February 2-4). These authors found that animals injected with 2-NBDG under fasting conditions (low serum glucose level) accumulated this probe in tumors, and uptake of 2-NBDG could be blocked under non-fasting conditions (high serum glucose level).

Additionally, U.S. Pat. No. 6,489,302 relates to a conjugate, comprising a saccharide and one or more therapeutic or diagnostic agents for treatment and diagnosis of cancer and viral disease which uses the GLUT pathway.

Near-infrared (NIR) dyes are presently attracting considerable interest as fluorescence probes for detection of cancer ((a) Lin, Y., Weissleder, R., and Tung, C. H. (2002) Novel near-infrared cyanine fluorochromes: synthesis, properties, and bioconjugation. *Bioconjugate Chem.* 13, 605-610. (b) Achilefu, S., Jimenez, H. N., Dorshow, R. B., Bugaj, J. E., Webb, E. G., Wilhelm, R. R., Rajagopalan, R., Johler, J., Erion, J. L. (2002) Synthesis, in vitro receptor binding, and in vivo evaluation of fluorescein and carbocyanine peptide-based optical contrast agents. *J. Med. Chem.* 45, 2003-2015. (c) Mujumdar, S. R., Mujumdar, R. B., Grant, C. M., and Waggoner, A. S. (1996) Cyanine-labeling reagents: sulfobenzindocyanine succinimidyl esters. *Bioconjugate Chem.* 7, 356-362) and as photosensitizers for cancer treatment by photodynamic therapy (PDT) (Dougherty, T. J., Gomer, C. J., Henderson, B. W., Jori, G., Kessel, D., Korbelik, M., Moan, J., and Peng, Q. (1998) Photodynamic therapy. *J. Natl. Cancer Inst.* 90, 889-905). Since tissue is relatively transparent to NIR light, NIR fluorescence imaging (NIRF) and PDT are capable of detecting and treating, respectively, even subsurface tumors. Owing to the need to increase photosensitizers' water solubility and to increase their affinity for tumor tissues, a great deal of effort has been devoted by many research groups to develop photosensitizers covalently linked with various carbohydrate moieties ((a) Sternberg, E. D., Dolphin, D. and Bruckner, C. (1998) Porphyrin-based photosensitizers for use in photodynamic therapy. *Tetrahedron* 54, 4151-4202. (b) Licha, K. (2002) Contrast agents for optical imaging. *Top. Cur. Chem.* 222, 1-29). However, none of them was intended to take advantage of the intracellular trapping mechanism for 2DG in tumor cells as it does for PDG.

A key limitation of cancer drugs is their lack of specificity for tumor cells. There is therefore a need to develop tumor-specific agents that are targeted at GLUT transporters, which constitute the main pathway that tumor cells utilize for import of substrates for energy production. Since glucose is the principal substrate for energy production utilized by most if not all tumors the agents which target this critical pathway should exhibit a substantially enhanced level of tumor specificity.

Stable bacteriochlorophyll (BChl) analogs derived from *R. Sphaeroides* are excellent NIR dyes for NIRF and PDT because of their favorable photophysical properties ($^1O_2$ yield: 45%) and long activation and fluorescence emission wavelengths (750-850 nm). (Pandey, R. K.; Zheng, G., Porphyrins as Photosensitizers in Photodynamic Therapy. In The Porphyrin Handbook, ed.; Kadish, K. M.; Smith, K. M.; Guilard, R., Eds. Academic Press: Boston, 2000; Vol. 6, pp 157-230.) Since native BChl is very unstable and undergoes rapid oxidation to the chlorin state (660 nm), preparation of a stable BChl analog is a synthetic challenge. In recent years, many approaches to remove the major points of fragility in the BChl a molecule have been tried by various investigators. These include replacing the central metal, magnesium, with other metal ions (e.g., palladium) to form stable complexes, (Fiedor, J.; Fiedor, L.; Kammhuber, N.; Scherz, A.; Scheer, H., Photodynamics of the bacteriochlorophyll-carotenoid system. 2. Influence of central metal, solvent and beta-carotene on photobleaching of bacteriochlorophyll derivatives. Photochemistry & Photobiology. 2002 August;76(2):145-52; Schreiber, S.; Gross, S.; Brandis, A.; Harmelin, A.; Rosenbach-Belkin, V.; Scherz, A.; Salomon, Y., Local photodynamic therapy (PDT) of rat C6 glioma xenografts with Pd-bacteriopheophorbide leads to decreased metastases and increase of animal cure compared with surgery. International Journal of Cancer. 2002 May 10;99(2):279-85.) modifying the isocyclic ring, and replacing the phytyl group at the propionyl residue either through transesterification or by conversion to the corresponding amide derivatives. (Rosenbach-Belldn, V.; Chen, L.; Fiedor, L.; Tregub, I.; Paviotsky, P.; Brumfeld, V.; Salomon, Y.; Scherz, A., Serine conjugates of chlorophyll and bacteriochlorophyll: photocytotoxicity in vitro and tissue distribution in mice bearing melanoma tumors. Photochemistry & Photobiology. 1996 July;64(1):174-81.) In particular, Pandey, et al. have shown that naturally occurring unstable BChl a (extracted from *Rb. Sphaeroides*) can be converted to the stable bacteriochlorins, bacteriopurpurin-18 and bacteriopurpurinimide. (Kozyrev, A. N.; Zheng, G.; Zhu, C. F.; Dougherty, T. J.; Smith, K. M.; Pandey, R. K., Syntheses of stable bacteriochlorophyll-a derivatives as potential photosensitizers for photodynamic therapy. Tetrahedron Letters 1996, 37, (36), 6431-6434; Chen, Y.; Graham, A.; Potter, W.; Morgan, J.; Vaughan, L.; Bellnier, D. A.; Henderson, B. W.; Oseroff, A.; Dougherty, T. J.; Pandey, R. K., Bacteriopurpurinimides: highly stable and potent photosensitizers for photodynamic therapy. Journal of Medicinal Chemistry. 2002 Jan. 17;45 (2):255-8.) In this approach, converting the fused isocyclic ring to a cyclic imide moiety enhanced the stability and solubility of the BChl analogs. Attachment of a variable allyl substituent to the imide moiety allowed the lipophilicity of the molecule to be fine-tuned. Some of these agents are highly potent against radiation-induced fibrosarcoma (RIF-1) in mice. In another elegant demonstration, Fiedor et al. found that inserting palladium into the BChl ring significantly improves its stability toward reactive oxygen species. (Fiedor, J.; Fiedor, L.; Kammhuber, N.; Scherz, A.; Scheer, H., Photodynamics of the bacteriochlorophyll-carotenoid system. 2. Influence of central metal, solvent and beta-carotene on photobleaching of bacteriochlorophyll derivatives. Photochemistry & Photobiology. 2002 August;76(2):145-52.) One such compound, Tookad®, is now under clinical evaluation for treating prostate cancer. To achieve higher levels of tumor selectivity, target-specific BChls derived from stable BChl suitable by bioconjugation are desired. For this purpose, a universal linker introduced into a stable BChl molecule that will facilitate binding of biomolecules such as peptides, proteins, and other affinity ligands is desirable. Accordingly, the present invention provides synthesis of novel functionalized BChl dyes containing an isothiocyanate moiety, their bioconjugatioh to cancer targeting agents, and the ini vivo optical imaging of animal tumors with these new bioconjugates.

SUMMARY OF THE IVENTION

The present invention relates to novel chemical compounds, referred to herein as 2-deoxyglucose conjugates or pharmaceutically acceptable salts thereof, in which a 2-deoxyglucose conjugate is represented by the formula:

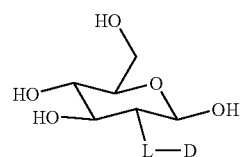

wherein L is a linker group; and D is a diagnostic or therapeutic agent, provided that said conjugate is not [$^{18}$F]deoxyglucose or 2-[N-(7-nitrobenz-2-oxa-1,3-diazol-4yl)amino]-2-deoxy-D-glucose.

In addition, the present invention provides methods of making the novel chemical compounds of the present invention.

The present invention also relates to pharmaceutical and veterinary compositions comprising one or more of the 2-deoxyglucose conjugates of the present invention, and one or more pharmaceutically acceptable diluents, carriers or excipients.

The invention further relates to a method of treating tumor disease in an animal, comprising administering one or more of the 2-deoxyglucose conjugates of the present invention to an animal in need thereof to treat the tumor disease of the animal.

DETAILED DESCRIPTION OF THE INVENTION

Figure 1:
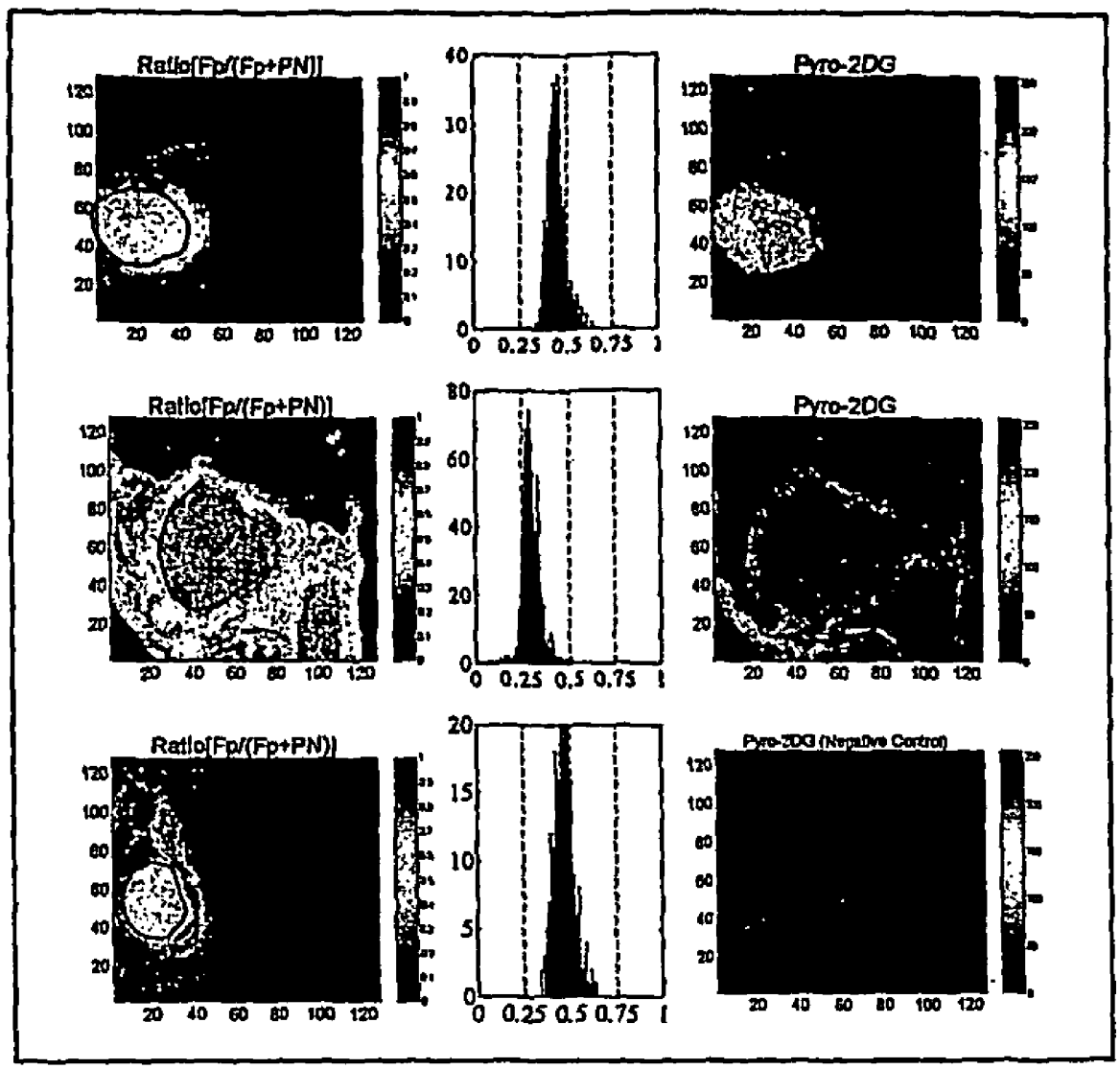
FIG. 1. Fluorescence images of drug control (top row: tumor+Pyro-2DG), normal tissue control (middle row: normal tissue of the same animal) and tumor control (bottom row, tumor alone) in 9L glioma bearing animals. Note: The tumor and normal muscle margin are outlined with a black circle in the redox ratio images (the first column), the redox ratio histograms corresponding to the marked region (black circle) are also presented here (the second column).

The invention relates to novel chemical compounds, referred to herein as 2-deoxyglucose conjugates, or pharmaceutically acceptable salts thereof, in which a 2-deoxyglucose conjugate is represented by the formula:

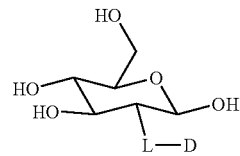

wherein L is a linker group; and D is a diagnostic or therapeutic agent, provided that said conjugate is not [$^{18}F$]deoxyglucose or 2-[N-(7-nitrobenz-2-oxa-1,3-diazol-4-yl)amino]-2-deoxy-D-glucose.

In a preferred embodiment, the linker group, L, is a covalent bond, —NH—, -peptide-, -nucleic acid-, —O—$CH_2$)$_r$—O—, —NH—$CH_2$—$CH_2$—NH—, —NH—CH(COOH)—$CH_2$—NH—, —NH—$CH_2$—CH(COOH)—NH—, —NH—$CH_2$— $CH_2$—$CH_2$—NH, —O—($CH_2$)$_r$—NH—, —S—($CH_2$)$_r$NH—, —S—($CH_2$)$_r$—C(O)—, —NH—$CH_2$—C(O)—, —O—$CH_2$$CH_2$—O—$CH_2$—O, —NH—NH—C(O)—$CH_2$—, —NH—C($CH_2$)$_2$—C(O), or —NH—NH—C(O)—($CH_2$)$_r$—C(O)NH—N=, wherein r, in each instance, is from 2-5. Preferably, the linker group, L, is susceptible to cleavage by cytosolic enzymes. Preferably, the linker group, L, is a peptide consisting of from about 1 to about 20 amino acids, more preferably about 1 to about 10 amino acids, and even more preferably about 1 to about 6 amino acids.

In further embodiments, the diagnostic or therapeutic agent, D, is a photosensitive agent, an oncotherapeutic agent, a tumor diagnostic agent, an anti-AIDS agent, an antioxidant, a antirheumatic, an antiallergic, an antianemic agent, an antibiotic, an antidiabetic, an antiemetic, an antihistamine, an antiepileptic, a β-receptor blocker, a calcium antagonist, an ACE inhibitor, a bronchodilating agent, an antiasthmatic, a cholinergic, a corticoid, a dermatic, a diuretic, an enzyme inhibitor, a gout remedy, an influenza remedy, a sedative, an immunotherapeutic agent, a hepato-therapeutic agent, an antilipemic, a migraine remedy, a muscle relaxant, an anesthetic, a neuropathy preparation, an antihyperkinetic agent, a psychoactive agent, a thyreotherapeutic agent, a sex hormone, a sex hormone inhibitor, an antispasmodic agent, a vitamin, a wound treating agent, an analgesic, an antimetabolite, a topoisomerase inhibitor, a radiosensitizer, an inhibitor of DNA repair or an α-sympathicomimetic.

Preferably, the photosensitive agent of the present invention is a near infrared dye selected from the group consisting of pyropheophorbide, cyclophosphamide, cyclophosphamide derivatives, bacteriochlorin (BChl) and bacteriochlorin derivatives, Cy5.5, Cy7, the hexyl ether analog of pyropheophorbide, the hexyl ether analog of pyropheophorbide carotenoid conjugate, benzothiazole (5P203), 4-hydroperoxy-cyclophosphamide (4HC), dicarbocyanine, and tricarbocyanines, such as NIR805, Indocyanine Green (ICG) and Cypate.

The invention also provides conjugates of 2-deoxyglucose, wherein the diagnostic or therapeutic agent is a photosensitive agent which is a photodynamic therapy agent, and preferably the photodynamic therapy agent is selected from the group consisting of a porphyrin, a chlorin, a bacteriochlorin, and derivatives thereof.

The diagnostic or therapeutic agent of the present invention may also be an oncotherapeutic agent. The oncotherapeutic agent is preferably cyclophosphamide, 4-hydroperoxycyclophosphamide, taxol, adriamycin, or temozolomide. In a preferred embodiment, the oncotherapeutic agent is 4-hydroperoxycyclophosphamide.

Figure 4:
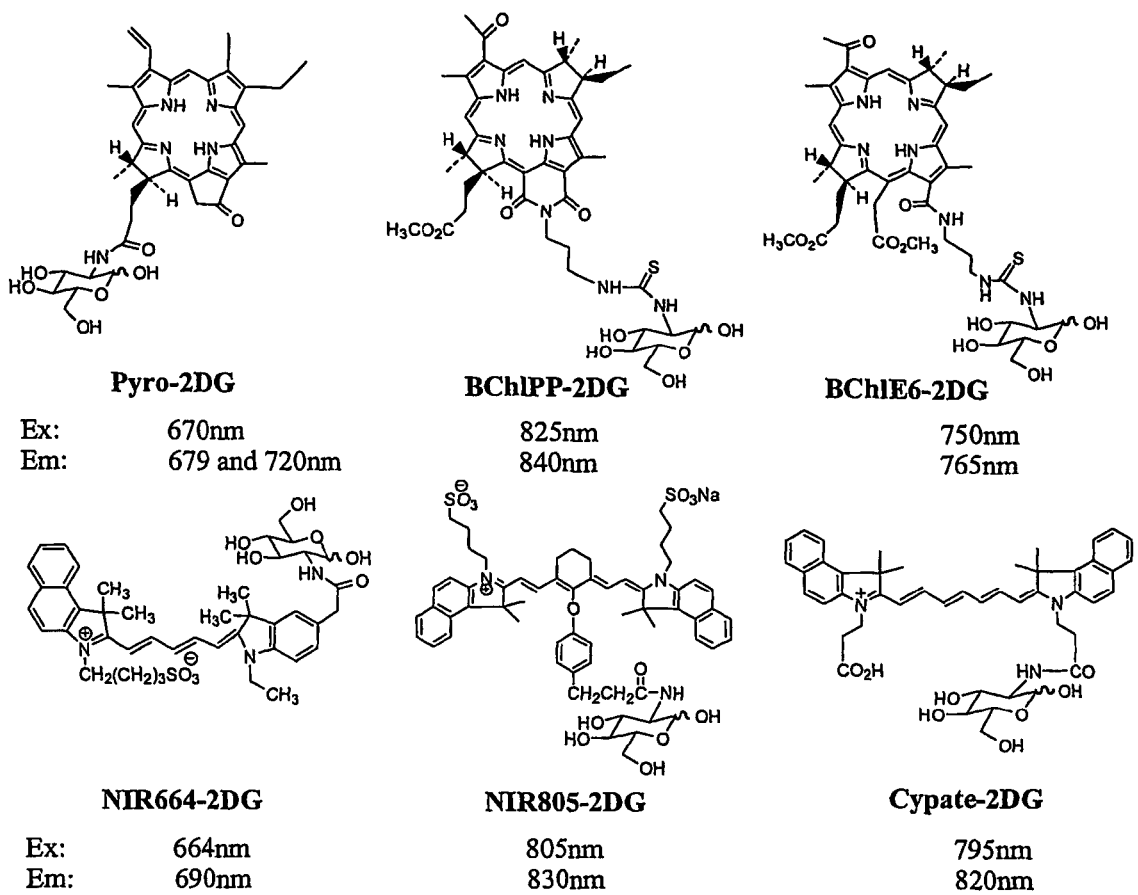
FIG. 4. 2-Deoxyglucose conjugates targeting GLUT.

Examples of 2-deoxyglucose conjugates encompassed by the present invention are shown in FIG. 4. The present invention is not limited to the compounds shown in FIG. 4, but rather these compounds are illustrative examples of conjugates encompassed herein.

The invention also provides a method of diagnosing tumor disease in an animal comprising administering one or more of the 2-deoxyglucose conjugates of the present invention to an animal in need thereof and detecting the presence of said conjugate in the animal.

The invention also provides a method of treating tumor disease in an animal, comprising administering one or more of the 2-deoxyglucose conjugates of the present invention to an animal in need thereof to treat the tumor disease of the animal. In one embodiment, the tumor is a glioma.

The invention also provides a method of treating disease in an animal using photodynamic therapy comprising administering one or more of the 2-deoxyglucose conjugates of the present invention to an animal in need thereof, followed by exposing the animal to ultraviolet, visible or infrared radiation to treat the disease of the animal. Preferably, the animal is exposed to near infrared radiation.

The specific dose and duration of light again will depend upon the photosensitizer chosen. The fluence rate applied is preferably about 25 to about 100 mW/cm$^2$, and most preferably about 50 to about 75 mW/cm$^2$, while the duration of light application is about 5 to about 60 minutes, and most preferably about 20 to about 30 minutes. Suitable sources of light include commercially available lasers, lamps, light emitting diodes and the like.

Preferably, LED arrays (Efos Canada, Inc., Mississauga, Ontario, Canada) are employed. To achieve the desired wavelength of light, the lamp may be equipped with commercially available filters.

Various photosensitizers for use in the present invention are useful over the range of 350 to 1300 nm, the exact range being dependent upon the particular photosensitizer. Preferred photosensitizers are those useful in the range of 650-1000 nm (i.e., in the near infrared ("NIR")). For example, pyropheophorbide and bacteriochloiin are useful in the 650-900 nm range.

It also is within the confines of the present invention that one or more quenchers can be administered before, during or after the administration of the conjugates of the present invention, but before application of light. Suitable quenchers include but are not limited to glutathione, trolox, flavonoids, vitamin C, vitamin E, cysteine and ergothioneine and other non-toxic quenchers, and preferably vitamin E. The amount of the quencher administered will depend upon the specific quencher(s) chosen and can be determined by one skilled in the art. However, when the quencher is vitamin E, the preferred dose ranges from about 10 mg/kg body weight to about 1 g/kg body weight, and most preferably about 100 mg/kg body weight. Administering one or more of the aforementioned quenchers is optional, and is complimentary to administering the conjugates of the present invention. Preferred complementary quenchers, such as -vitamin E, quench free radical formation generated from a Type I photoreaction via electron transfer, and may be used as a complementary protection mechanism to quenching singlet oxygen that is generated from a Type II photoreaction via energy transfer. Nevertheless, singlet oxygen is the major cytotoxic agent responsible for PDT.

In one embodiment of the present invention, the artificial irradiation is applied from about 5 minutes to about 3 hours after administering one or more types of conjugates of the present invention. Preferably, the artificial irradiation is applied about 10 to about 60 minutes after administering one or more kinds of conjugates of the present invention.

The light should be applied at a sufficient wavelength, dose and duration to maximize the tumor damage, and, at the same time, to minimize the damage to the red blood cells and/or other surrounding tissue.

In embodiments, the invention is directed to a method of inhibiting the growth of cancer cells, in vitro or in vivo, comprising contacting cancer cells with a conjugate of the present invention and, in the case of a conjugate containing a photodynamic therapy agent, exposing the cancer cells to an effective amount of artificial irradiation. In one aspect, the invention provides methods of inhibiting the growth of cancer cells, such as breast, lung, pancreas, bladder, ovarian, testicular, prostate, liver, retinoblastoma, Wilm's tumor, adrenocarcinoma or melanoma, and preferably, the cancer tumor is a prostate cancer tumor.

In embodiments, in the methods of the present invention, the artificial irradiation is selected from the group consisting of artificial ultraviolet, infrared (IR), gamma-irradiation, x-ray and visible light. Preferably, the artificial irradiation is IR, and even more preferably, the artificial irradiation is near-infrared (NIR).

In the methods of the present invention, in embodiments the artificial irradiation is applied about 30 minutes to about 48 hours after administering the conjugate of the present invention (e.g., by injection), and even more preferably, about 3 to about 24 hours after administering the conjugate of the present invention. Preferably, the light dose is 10 mW/cm$^2$-100 mW/cm$^2$.

In a separate embodiment, in the methods of the present invention, it is preferred that the artificial irradiation be applied for about 5 seconds to about 60 minutes, even more preferred is that the artificial irradiation be applied for about 1 minute to about 45 minutes, and most preferably, in the methods of the present invention, the irradiation is applied for about 10 to about 30 minutes.

The present invention also provides a method for curing a subject suffering from a cancer. In the cancer treating methods of the present invention, the subject may be a primate, (human, ape, chimpanzee, gorilla or monkey) dog, cat, mouse, rat, rabbit, horse, goat, sheep, cow, chicken. The cancer may be identified as a breast, lung, pancreas, bladder, ovarian, testicular, prostate, liver, retinoblastoma, Wilm's tumor, adrenocarcinoma or melonoma. This method comprises administering to the subject a cancer killing amount of one or more conjugates of the present invention.

Also provided is a method of inhibiting the proliferation of mammalian tumor cells which comprises contacting the mammalian tumor cells with a sufficient concentration of the conjugate of the invention, followed by exposure to artificial irradiation, so as to inhibit proliferation of the mammalian tumor cells.

The subject invention further provides methods for inhibiting the growth of human tumor cells, treating a tumor in a subject, and treating a proliferative-type disease in a subject. These methods comprise administering to the subject an effective amount of the conjugate of the invention.

It is apparent therefore that the present invention encompasses pharmaceutical compositions, combinations and methods for treating human carcinomas. For example, the invention includes pharmaceutical compositions for use in the treatment of human carcinomas comprising a pharmaceutically effective amount of the conjugate of the present invention and a pharmaceutically acceptable carrier.

The compositions may additionally include other drugs or antibodies treating carcinomas.

The compositions of the invention may be in a variety of dosage forms which include, but are not limited to, liquid solutions or suspension, tablets, pills, powders, suppositories, polymeric microcapsules or microvesicles, liposomes, and injectable or infusible solutions. The preferred form depends upon the mode of administration and the therapeutic application.

The compositions of the invention also preferably include conventional pharmaceutically acceptable carriers and adjuvants known in the art such as human serum albumin, ion exchangers, alumina, lecithin, buffer substances such as phosphates, glycine, sorbic acid, potassium sorbate, and salts or electrolytes such as protamine sulfate.

The most effective mode of administration and dosage regimen for the compositions of this invention depends upon the severity and course of the disease, the patient's health and response to treatment and the judgment of the treating physician. Accordingly, the dosages of the compositions should be titrated to the individual patient. Nevertheless, an effective dose of the compositions of this invention may be in the range of from about 1 to about 2000 mg/kg. Preferably, the dosage is from about 2 to about 1000 mg/kg, more preferably, 4 to about 400 mg/kg, and even more preferably, 5 to about 100 mg/kg.

The interrelationship of dosages for animals of various sizes and species and humans based on mg/kg of surface area is described by Freireich, E. J. et al., Cancer Chemother. 50 (4): 219-244 (1966). Adjustments in the dosage regimen may be made to optimize the tumor cell growth inhibiting and killing response, e.g., doses may be divided and administered on a daily basis or the dose reduced proportionally depending upon the situation (e.g., several divided doses may be administered daily or proportionally reduced depending on the specific therapeutic situation).

It would be clear that the dose of the composition of the invention required to achieve cures may be further reduced with schedule optimization.

In accordance with the practice of the invention, the pharmaceutical carrier may be a lipid carrier. The lipid carrier may be a phospholipid. Further, the lipid carrier may be a fatty acid. Also, the lipid carrier may be a detergent. As used herein, a detergent is any substance that alters the surface tension of a liquid, generally lowering it.

In one example of the invention, the detergent may be a nonionic detergent. Examples of nonionic detergents include, but are not limited to, polysorbate 80 (also known as Tween 80 or (polyoxyethylenesorbitan monooleate), Brij, and Triton (for example Triton WR-1339 and Triton A-20).

Alternatively, the detergent may be an ionic detergent. An example of an ionic detergent includes, but is not limited to, alkyltrimethylammonium bromide.

Additionally, in accordance with the invention, the lipid carrier may be a liposome. As used in this application, a "liposome" is any membrane bound vesicle which contains any molecules of the invention or combinations thereof.

The amount of conjugate administered in the formulation will depend upon the photosensitizer chosen. Preferably, the amount of conjugate administered is about 0.1 to about 10.0 mg/kg body weight of the subject, more preferably about 0.3 to about 6 mg/kg body weight, and even more preferably, 0.4-4.0 mg/kg body weight.

In embodiments, in the methods of treating cancer of the present invention, the artificial irradiation is applied for about 10 seconds to about 60 minutes, and even more preferably; the artificial irradiation is applied for about 15 seconds to about 30 minutes.

In a separate embodiment, the present invention further provides pharmaceutical compositions which comprise the conjugates of the present invention and a pharmaceutically acceptable carrier.

The present invention further provides a method of treating cancer in a subject cancer comprising administering a therapeutically effective amount of the pharmaceutical composition of the present invention.

The antineoplastic agents of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A., Ed., Mack, Easton Pa., 1980). In order to form a pharmaceutically acceptable composition suitable for effective administration, such compositions will contain an effective amount of the compound, together with a suitable amount of carrier vehicle.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

"Administering" refers providing at least one pharmaceutical agent to a subject. Thus, "administering" includes oral administration, administration as a suppository, topical contact, intravenously, intraperitoneally, intramuscularly, subcutaneously, intranasally, enterally, parenterally, implantation of a slow release device such as a miniosmotic pump, and inhalation. When administering by injection, the administration may be by continuous infusion, or by single or multiple boluses.

In providing a mammal, and particularly a human, with therapeutic agents, the dosage will vary depending upon such factors as the recipient's age, weight, height, sex, general medical condition, previous medical history, etc. In general, it is desirable to provide the recipient with a dosage in the range of from about 1 pg/kg to about 10 mg/kg (body weight of recipient), although a lower or higher dosage can be administered. The dosage frequency can be repeated at intervals ranging from each day to every other month.

The compounds of the present invention are intended to be provided to recipient subjects in an amount sufficient to induce a therapeutic effect. An amount is said to be sufficient to induce a therapeutic effect if the dosage, route of administration, etc. of the agent are sufficient to reduce, attenuate, or stop tumor progression.

The compounds of the invention may be administered either alone or in combination with additional therapeutic agents. The administration of such agent(s) may be for either a "prophylactic" or "therapeutic" purpose. When provided prophylactically, the agents are provided in advance of any tumor detection. The prophylactic administration of the compound(s) serves to prevent or attenuate any tumor formation. When provided therapeutically, the agent(s) is provided at (or shortly after) the detection of actual tumor formation.

The compositions of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, are described, for example, in Remington's Pharmaceutical Sciences, 18th edition, A. R. Gennaro, Ed., Mack Pub., Easton, Pa., 1990.

"Pharmaceutically acceptable carrier" includes any material which when combined with a therapeutic agent, retains the therapeutic agent's activity and is nonreactive with the mammal's immune system. Examples include, but are not limited to, any of the standard pharmaceutical carriers such as a phosphate buffered saline solution, water, emulsions such as oil/water emulsion, and various types of wetting agents. Other carriers may also include sterile solutions, tablets, including coated tablets, and capsules. Typically, such carriers contain excipients, such as starch, milk, sugar certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

Additional pharmaceutical methods may be employed to control the duration of action. Control release preparations may be achieved through the use of polymers to complex or absorb therapeutic agents. The controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate the therapeutic agent(s) into particles of a polymeric material such as polyesters, polyamino acids, hydrogels, poly (lactic acid) or ethylene vinylacetate copolymers. Alternatively, instead of incorporating these agents into polymeric particles, the therapeutic agent(s) can be entrapped in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin micro spheres, microemulsions, nanoparticles, and nanocapsules or in macroemulsions. Such techniques are disclosed in Remington's Pharmaceutical Sciences, 18th edition, A. R. Gennaro, Ed., Mack Publ., Easton, Pa. (1990).

The present invention also provides methods of maiiing the compounds of the present invention. In embodiments, the present invention provides a method of making 2-deoxyglucose derivatives of the diagnostic and therapeutic agents of the present invention.

In particular embodiments, the synthesis of a 2-deoxyglucose derivative of pyropheophorbide is provided. For example, to synthesize the desired Pyro-2DG, pyropheophorbide is first treated with N-hydroxysuccinimide in the presence of DCC. The pyropheophorbide succinimidyl ester so obtained is then reacted with activated D-glucosamine. to yield the desired conjugate in 50% overall yield (see Scheme 1'). In embodiments, activated D-glucosamine is produced by treating D-glucosamine hydrochloride with sodium methoxide.

In further embodiments, an amine reactive universal linker, such as isothiocyanate, is introduced into the bacteriochlorophyll (BChl) macrocycle allowing bioconjugation of these NIR dyes with biologically important molecules such as peptides, metabolites, proteins, and other affinity ligands.

In further embodiments, the synthesis of bacteriochlorin $e_6$ isothiocyanate (BChlE6-NCS) is also provided. BChlE6-NCS can subsequently be conjugated to a 2-deoxyglucose moiety to form bacteriochlorin $e_6$ 2-deoxyglucosamide. Specifically BOC-protected amino-bacteriochlorin $e_6$ (BChlE6-BOC) is formed from bacteriopheophorbide as described in more detail below. The bacteriopheophorbide α methyl ester is then used to produce amino-bacteriochlorin e6 (BchlE6-NH2) and bacteriochlorin e6 isothiocyanate (BChlE6-NCS), which is then conjugated to form BChlE6-2DG.

The examples below explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

EXAMPLES

Example 1

Experimental Procedures

Materials and General Methods. Melting points are uncorrected. UV-vis spectra were recorded on a Beckman DU-600 spectrophotometer. Fluorescence emission was measured with a Perkin-Elmer LS-50B fluorometer. $^1$H NMR spectra were recorded on a Bruker ASPECT 360 MHz instrument. ESI-MS and HRMS spectrometric analysis were performed at the Mass Spectrometry Facility of the Department of Chemistry, University of Pennsylvania. Methyl pheophorbide α was isolated from *Spirulina pacifica* algae available from Cyanotech Corp., Hawaii. Pyropheophorbide (1) was synthesized from methyl pheophorbide according to literature procedures (Zheng, G., Li, H., Zhang, M., Chance, B., and Glickson, J. D. (2002) Low-density Lipoprotein Reconstituted by Pyropheophorbide Cholesteryl Oleate as Target Specific Photosensitizer *Bioconjugate Chem.* 13, 392-396). Other chemicals were purchased from Aldrich. When necessary, solvents were dried before use. For TLC, EM Science TLC plates (silica gel 60 $F_{254}$) were used. Reverse phase (RP) analytical HPLC was performed using a Zorbax RX-C8 (9.4 mm×250 mm) column eluting at 1.0 mL/min with MeCN/phosphate buffer (0% to 99% MeCN gradient) with UV-vis detection at 414 nm.

Pyropheophorbide succinimidyl ester (2): Pyropheophorbide (1) (208 mg 0.39 mmol) was activated with DCC (80 mg 0.39 mmol) and N-hydroxysuccinimide (92 mg 0.8 mmol) in 10 mL DMF. After stirring for 24 h, urea was filtered off, and solvents were removed. The crude product was purified by column chromatography (silica gel 60) and eluted with 5% methanol in $CH_2Cl_2$. The desired product was crystallized from $CH_2Cl_2$/hexane in 80% yield (195 mg 0.31 mmol). Mp: 200-202° C. UV-vis in $CH_2Cl_2$: 413 nm (ε $1.1×10^5$), 509 ($1.2×10^4$), 538 ($1.0×10^4$), 609 ($8.7×10^3$) and 666 (5.0 ×$10^4$). Mass calculated for $C_{37}H_{37}N_5O_5$: 631.7; found by ESI-MS 632.7($MH^+$) and 654.6 ($M+Na^+$). $^1$H NMR ($CDCl_3$, δ ppm): 9.42, 9.31 and 8.56 (each s, 1H, 5-H, 10-H and 20-H); 7.95 (dd, J=17.8, 11.8 Hz, 1H, $3^1$-CH=$CH_2$); 6.25 (d, J=17.8 Hz, 1H, trans-$3^2$-CH⊚$CH_2$); 6.14 (d, J=11.8 Hz, 1H, cis-$3^2$-CH=$CH_2$); 5.17 (ABX, 2H, $13^2$-$CH_2$); 4.49 (d, J=7.2 Hz, 1H for 18-H); 4.40 (m, J=7.2 Hz, 1H for 17-H); 3.63 (s, 5H, 8-$CH_2CH_3$, 12-$CH_3$); 3.40 and 3.18 (each s, 3H, 2-$CH_3$ and 7-$CH_3$); 2.87 (br, 5H, $17^1$-H and succinimide-$CH_2CH_2$—); 2.62 and 2.27 (each m, 1H, for 2×$17^2$-H); 1.93 (m, 1H for $17^1$-H); 1.82 (d, J=7.2 Hz, 3H, 18-$CH_3$); 1.70 (t, J=7.2 Hz, 3H, 8-$CH_2CH_3$); 1.33 and 1.12 (each brs, 1H, 2×N—H).

Pyropheophorbide-2-deoxyglucosamide (Pyro-2DG) (3): D-Glucosamine hydrochloride (130 mg 0.6 mmol) was added to a solution of sodium methoxide (32.4 mg 0.6 mmol) in 7 mL DMSO. The mixture was stirred for 2 h, and pyropheophorbide succinimide ester (2) (190 mg 0.3 mmol) was added. The reaction mixture was stirred under argon atmosphere for 20 h. After removing solvents, the crude product was washed with dichloromethane, water and crystallized from methanol. The title compound was obtained in 102 mg yield. The filtrate was further concentrated and purified by silica gel plate chromatography (20% methanol in dichloromethane), 30 mg more of Pyro-2DG was obtained. Thus, the total product yield is 63% (132 mg, 0.19 mmol). Mp: >200° C. Analytical RP HPLC: $R_t$ 20.9 min, 99.5%. UV-vis in DMSO: 415 nm (ε $1.2×10^5$), 510 ($1.2×10^4$), 540 ($1.0×10^4$), 611 ($8.6×10^3$) and 668 ($5.0×10^4$). Mass calcd for $C_{39}H_{45}N_5O_7$: 718.3217 ($M+Na^+$), found by HRMS: 718.3249 ($M+Na^+$). $^1$H NMR (DMSO-$d_6$): 8.97, 8.70 and 8.69 (each s, 1H, 5-H, 10-H, and 20-H); 7.97 (dd, J=17.7, 11.8 Hz, 1H, $3^1$-CH=$CH_2$); 6.15 (dd, 2H, J=17.7 Hz, 1H, trans-$3^2$-CH=$CH_2$, J=5.4 Hz, α-H); 5.97 (d, J=11.8 Hz, 1H, cis-$3^2$CH=$CH_2$); 4.98 (ABX, 2H, $13^2$-$CH_2$); 4.81-4.35 (each m, total 5H, sugar-H); 4.18 (br, 1H for 18-H); 4.11 (d, J=7.2 Hz, 1H for 17-H); 3.68 (q, J=7.4 Hz, 2H, 8-$CH_2CH_3$); 3.58, 3.43 and 3.16 (s, each 3H, 12-$CH_3$, 2-$CH_3$ and 7-$CH_3$); 2.59 (m, 1H, $17^1$-H); 2.50 (m, 2H, $17^2$-H); 2.12 (m, 1H, $17^1$-H) 1.80 (d, J=7.2 Hz, 3H, 18-$CH_3$); 1.59 (t, J=7.2 Hz, 3H, 8-$CH_2CH_3$).

Confocal Microscopic Studies: 9L glioma cells were grown for 5 days in 4-well Lab-Tek chamber slides (Naperville, Ill.). Before the cell experiments, the culture medium was replaced by preincubation medium (medium with 1% (w/v) BSA instead of FBS). The cells were washed three times with preincubation medium (for 15, 15, and 30 min), and cultured in this medium for a further 20 hours. Experiments were started, after two quick washes with preincubation medium, by the addition of preincubation medium containing the indicated amounts of Pyro-2DG and/or D-Glucose. After 30 minutes incubation at 37° C., the cells were washed five times with ice-cold PBS containing 0.8% BSA, two times with PBS alone, and fixed for 20 minutes with 2% formaldehyde in PBS at room temperature. Then the chamber slides were mounted and sealed for confocal microscopic analysis.

Animals: Rat 9L glioma was implanted on the flanks of male Fisher 344 rats (150 -200 g) via subcutaneous injection of 0.1 mL, ~$10^6$ 9L glioma cells. Within ten days, tumors grew to the desired size of 1 cm in diameter.

After not feeding animals for 24 hours, the rats were anaesthetized via intraperitoneal injection of Ketamine (75 mg/kg) and Xylazine (10 mg/kg). Pyro-2DG (2 mL, concentration: 0.25 mg/mL) was injected via tail vein infusion over a period of 1 hour (dose: 2.5 mg/kg). Thirty minutes later, the rats were anesthetized again and subjected to PDT.

PDT Protocol: A "point treatment" protocol was designed for evaluating PDT response of Pyro-2DG. PDT was carried out using a KTP YAG pumped dye module (Laserscope, San Jose, Calif.) tuned to produce 670 nm light. Light delivery was through a 1 mm fiber to create a treatment spot of 0.96 mm in diameter when the fiber was held closely adjacent to the tumor. The light field was fixed in position at the center of the tumor by mounting the fiber in the center of a circular plate which was glued to the anesthetized animal. The light was delivered at a fluence rate of 75 mW/$cm^2$ to a total dose of 175 J/$cm^2$. Laser power output was measured with a power meter (Coherent, Auburn, Calif.).

Fluorescence Imaging of Tumors (Quistorff, B., Haselgrove, J. C., and Chance, B. (1985) High spatial resolution readout of 3-D metabolic organ structure: an automated, low-temperature redox ratio-scanning instrument. *Anal. Biochem.* 148, 389-400; Gu, Y. Q., Qian, Z. Y., Chen, J. X., Blessington, D., Ramanujam, N., and Chance, B. (2002) High-resolution three-dimensional scanning optical image system for intrinsic and extrinsic contrast agents in tissue. *Rev. Sci. Instruments* 73, 172-178; Ramanujam, N., Richards-Kortum, R., Thomsen, S., Mahadevan-Jansen, A., Follen M., and Chance B. (2001) Low temperature fluorescence imaging of freeze-trapped human cervical tissues. *Opt. Express* 8, 335-343): Immediately after PDT, animals were immersed in pre-cooled isopentane (−150° C.) and transferred to liquid nitrogen (−196° C.) 5 minutes later. Tumors were then surgically excised, embedded in a mixture of ethanol-glycerol-water (freeze point: −30° C.), and mounted at low temperature for 3D surface fluorometric scanning. Thus, the frozen tumor sample was milled flat and imaged every 100 μm from the top surface to the bottom of the tumor. The light guide (fused silica, 50 μm core diameter) stepped across the tissue surface at a fixed distance from the tissue surface (70 μm). The imaging resolution of the low temperature scanning fluorometer was 80μm. The fluorescent signals of FP (filters: Ex: 440DF20, Em: 520DF40), PN (filters: Ex: 365HT25, Em: 455DF70), Pyro-2DG (filters: Ex: 405DF40, Em: 700ALP) were imaged for each depth of tumor. The scanning was performed at 128×128 steps that could cover 1.024×1.024 cm². The fluorescence signal was automatically digitized and recorded on a PC. The redox ratio of FP/(FP+PN) was calculated with MATLAB.

To synthesize the desired Pyro-2DG, the pyropheophorbide was first treated with N-hydroxysuccinimide in the presence of DCC. The pyropheophorbide succinimidyl ester (2) so obtained was reacted with D-glucosamine that was activated by treating D-glucosamnine hydrochloride with sodium methoxide to yield the desired conjugate (3) in 50% overall yield (see Scheme 1'). The structures of all new compounds were confirmed by HRMS and NMR spectroscopy. The HPLC chromatograms of the final conjugate confirmed its homogeneity.

Despite containing the hydrophilic 2DG moiety, Pyro-2DG is only partially water-soluble due to the hydrophobic nature of the porphyrin macrocycle. Formulation with detergent (1% Tween 80) made it completely miscible with water and suitable for in vivo administration. A "point treatment" protocol for evaluating PDT response of Pyro-2DG was designed. Instead of irradiating the whole tumor area (1 cm in diameter), only an area ~1 mm in diameter at the center of the tumor was treated. The same laser power and light dose (75 mW/cm², 175 J/cm²) were used throughout the experiments. Based on the absorption and emission maxima of Pyro-2DG ($\lambda_{ex}$=665 nm; $\lambda_{em}$=720 nm), the 9L tumor was treated with 670 nm laser light, and a 700 nm long pass filter was incorporated into the 3D fluorescence scanner for collecting the Pyro-2DG fluorescence at 720 nm. This point treatment procedure is designed for two purposes: 1) to allow the adjacent untreated tumor region along with the normal tissue region to serve as internal controls; and 2) to evaluate possible bystander effects.

Scheme 1'. Synthesis of Pyro-2DG.

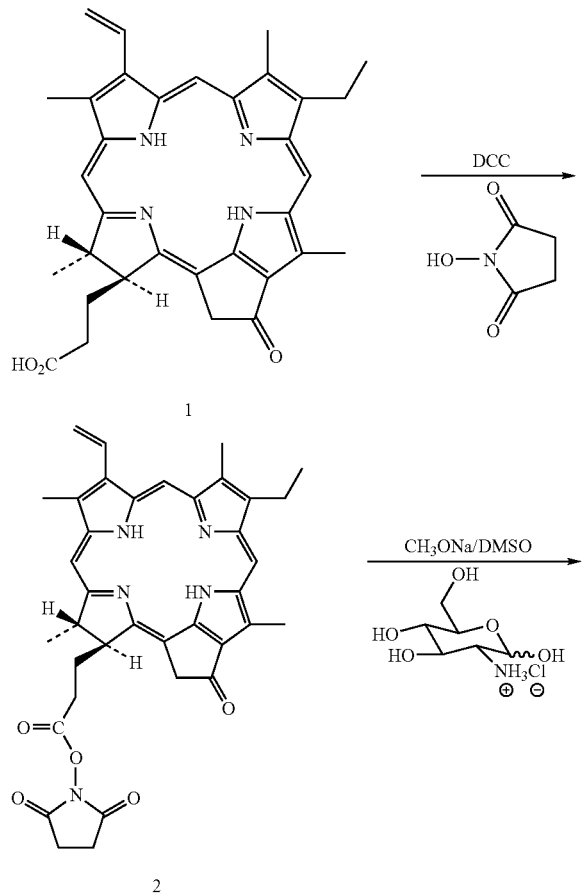

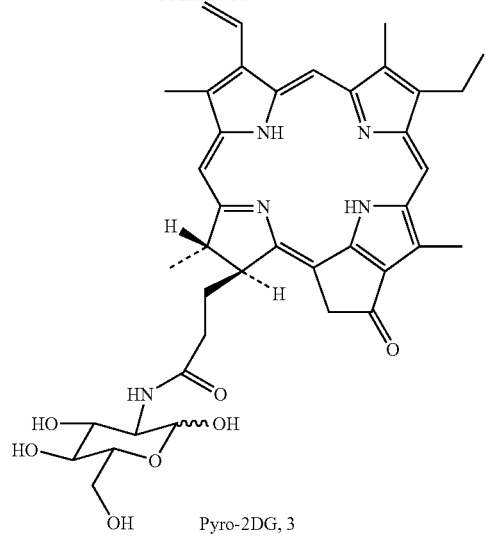

Pyro-2DG, 3

The tumor specificity of Pyro-2DG is, of course, limited by uptake of glucose by various normal tissues; however, most tumors consume substantially more glucose than the surrounding normal tissues. Thus, all PDT experiments were carried out under fasting conditions. Low serum glucose levels were achieved by not feeding animals for 24 hour before the experiments. Moreover, the animals were given low concentration Pyro-2DG via tail vein infusion over a period of 1 hour to enhance the tumor uptake. Thirty minutes after injection, the animals were subjected to the PDT (75 mW/cm², 175 J/cm²). After PDT, animals were rapidly frozen and kept in liquid nitrogen for fluorescence imaging studies using the low temperature 3D scanning fluorometer.

This fluorometer was designed originally to examine the redox state of in-vivo-freeze-trapped tissue (Quistorff, B., Haselgrove, J. C., and Chance, B. (1985) High spatial resolution readout of 3-D metabolic organ structure: an automated, low-temperature redox ratio-scanning instrument. Anal. Biochem. 148, 389-400). It detects the intrinsic fluorescence of oxidized flavoprotein (FP, $\lambda_{ex}$: 436 nm, $\lambda_{em}$: 560 nm) and reduced pyridine nucleotide (PN, $\lambda_{ex}$: 366 nm, $\lambda_{em}$: 450 nm) stemming from mitochondria. The PN signal indicates mainly NADH, whereas the FP signal originates from the flavins of dehydrolipoamide dehydrogenase component of pyruvate dehydrogenase and α-ketoglutarate dehydrogenase. Because 1) the flavoproteins are coupled to the mitochondrial NAD/NADH redox system by pyruvate dehydrogenase and α-ketoglutarate dehydrogenase reactions, and 2) only the reduced form of the PN system and the oxidized species of FP couple are strongly fluorescent, the ratio of FP/(FP+PN) calculated from FP and PN signals accurately represents the redox state of the mitochondrial NAD/NADH redox couple (Chance, B., Schoener, B., Oshino, R., Itshak, F., and Nadase, Y. (1979) Oxidation-Reduction Ratio Studies of Mitochondria in Freeze-Trapped Samples. J. Biol. Chem. 254, 4764-4771). Thus, the redox ratio can be used to evaluate the PDT damage to the tumor mitochondria. In addition to monitoring the fluorescence of endogenous PN (NADH) and FP, this fluorometer is also useful in detecting any exogenous fluorophore (e.g. Pyro-2DG) that is present in the specimen.

There are some distinctive advantages of this freeze-quenching technique (Quistorff, B., Haselgrove, J. C., and Chance, B. (1985) High spatial resolution readout of 3-D metabolic organ structure: an automated, low-temperature redox ratio-scanning instrument. *Anal. Biochem.* 148, 389400, Chance, B., Schoener, B., Oshino, R., Itshak, F., and Nadase, Y. (1979) Oxidation-Reduction Ratio Studies of Mitochondria in Freeze-Trapped Samples. *J. Biol. Chem.* 254, 4764-4771). First, it stops metabolic processes, providing a "snap shot" of metabolism at the moment of freezing and also allowing a 3D analysis by means of reflectance spectrophotometric imaging of successive slices through the frozen tissue block. Furthermore, the fluorescence quantum yield is typically 5- to 10-fold higher at liquid nitrogen temperature, vastly improving the signal-to-noise ratio. Also, because of the complete arrest of metabolic processes, the time taken for the analysis is not of importance. This facilitates high resolution scanning with signal/noise enhancement through signal averaging. Using this technique, we have studied fluorescence images of FP, PN (NADH) and Pyro-2DG on animals with or without PDT treatment. The results are discussed below:

FIG. 1 shows the redox ratio images (the first column), their corresponding histograms (the second column) and the Pyro-2DG fluorescence images (the third column) of 9L glioma and surrounding muscle tissue. The x and y axes of images represents the number of pixels scanned, whereas x and y axes of the histograms represents the relative redox ratio value and its corresponding pixel number, respectively. As shown in FIG. 1, Pyro-2DG is selectively accumulated inside the tumor margin (top row images) compared to surrounding normal tissue such as muscle (middle row images), and there is no background fluorescence observed from the control experiment in which tumor is imaged in the absence of Pyro-2DG (bottom row images). This study also demonstrates that the tumor control (tumor alone) and the drug control (yro-2DG+tumor) exhibit similar redox states since similar FP and PN signals and similar FP/(FP+PN) ratios were detected in both instances. This indicates that the addition of Pyro-2DG has no effect on the mitochondrial activities of the tumor in the absence of light.

Figure 2:
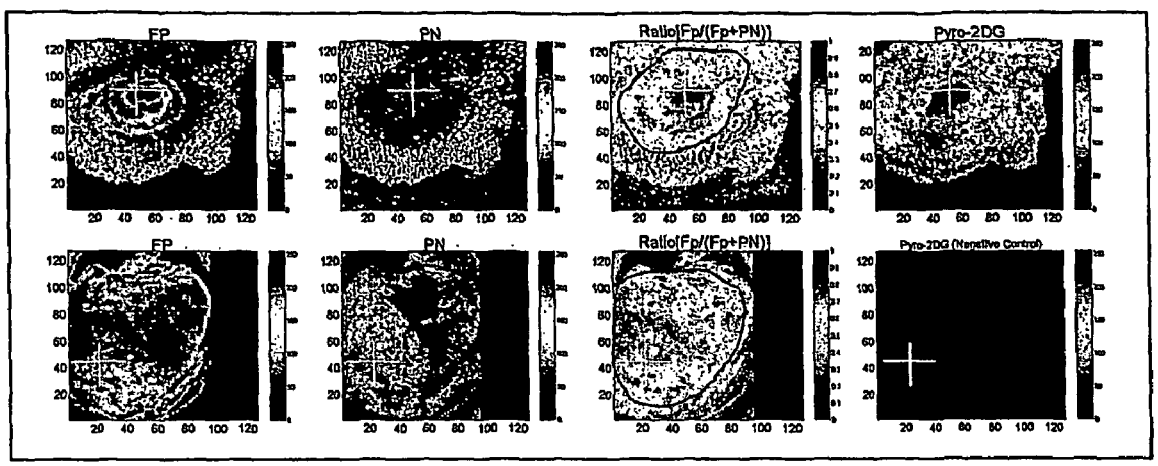
FIG. 2. Selective tumor destruction by PDT corresponds to a marked change in the intrinsic fluorescence of tumors (decreased NADH, increased PP) and the selective photobleaching of Pyro-2DG. (Top row: PDT of tumor with Pyro-2DG; bottom row: light control, PDT of tumor without Pyro-2DG). Note: The irradiated region is marked as a white cross, and the tumor margin is outlined with a black circle in both experiments.
Figure 3:
FIG. 3. Confocal microscopy images of 9L glioma cells incubated with 50 μM Pyro-2DG for 30 min at 37° C. in the absence (upper) and presence (lower) of 50 mM D-glucose. Left hand: fluorescence images; middle: bright field images; right hand: overlapping images.
Figure 3:
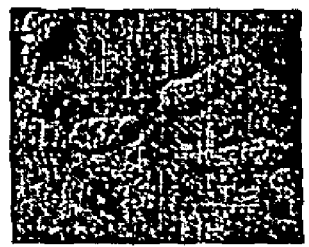
Figure 3:
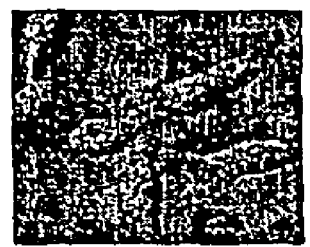
Figure 3:
Figure 3:
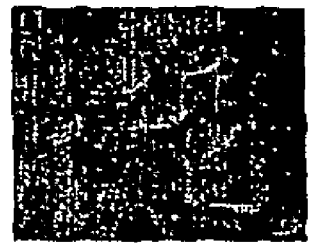
Figure 3:

Upon PDT treatment, Pyro-2DG dramatically altered the redox state of the tumor. As shown in FIG. 2, the irradiated spot (indicated by a cross) exhibited a marked increase in PP fluorescence (red region in the center of tumor, see the first image of the top row) and a significant decrease in NADH fluorescence (see the second image of the top row). This produced a dramatic increase in the redox ratio of the tumor [FP/(FP+PN), see the third image of the top row]. Since the ratio of FP/(FP+PN) represents the redox state of the mitochondrial NAD/NADH redox couple, the significant enhancement of this ratio clearly reflects the extensive mitochondrial damage (oxidation) experienced by the irradiated region of the tumor, but not the adjacent unirradiated region. Strikingly, the complete disappearance of the Pyro-2DG fluorescence signal was observed in the same region (there is a dark "hole" at the center of the tumor, see the last image of the top row), indicating selective photobleaching of the photosensitizer. Since PDT is mediated by the production of reactive oxygen species resulting in cell kill via oxidation (22), there is a direct correlation between the selective photobleaching of the Pyro-2DG and the selective tumor destruction stemming from the oxidation of tumor mitochondria. In order to verify that such tumor destruction is caused by the photodynamic action of the Pyro-2DG, a PDT control experiment was conducted by not injecting the photosensitizer. As shown in FIG. 2 (see the bottom row images), there is little or no change in the redox ratio in the absence of Pyro-2DG; this experiment, therefore, clearly demonstrates that the PDT response is due to Pyro-2DG' photosensitization.

To determine the specificity of Pyro-2DG toward GLUTs, confocal fluorescence microscopy studies were performed. As shown in FIG. 4, Pyro-2DG localizes within 9L glioma cells at 37° C. and that localization was competitively inhibited by D-glucose. In contrast to Pyro-2DG, uptake of pyropheophorbide a in 9L glioma cells is concentration dependent and is not inhibited by D-glucose, indicating that its uptake is GLUT-independent (data not shown). This study suggests that Pyro-2DG is delivered and trapped in tumor cells via the GLUT/hexokinase pathway.

In conclusion, a new photosensitizer targeted at the GLUT pathway to serve as both a targeted PDT agent and a NIR imaging agent has been designed and synthesized. Following intravenous administration to 9L glioma bearing animals, Pyro-2DG selectively accumulated in the tumor compared to the surrounding normal tissue as observed by measuring its NIR fluorescence at 720 nin using a low-temperature 3D fluorescence scanner. Upon PDT treatment of this tumor, this agent efficiently causes selective mitochondrial damage to the region of a tumor that was photoirradiated after administration of this agent, but does not affect tissues photoirradiated in the absence of the agent or tissues treated with the agent that are not photoirradiated. The confocal microscopy data are consistent with the hypothesis that Pyro-2-DG has been delivered and trapped in tumor cells via the GLUT/hexokinase pathway, and therefore, Pyro-2DG is useful both as a tumor-selective NIR fluorescence imaging probe and as a PDT agent.

Example 2

Experimental Procedures
Materials

All 2-deoxyglucose conjugates,. including pyropheophorbide 2-deoxyglucosamide (Pyro-2DG) (Zhang, M., et al., *Bioconjugate Chemistry* 14:709-714 (2003)), two bacteriochlorophyll 2-deoxyglucosamides (BChlPP-2DG and BChlE6-2DG), dicarbocyanine 2-deoxyglucosamide (NIR6642DG) and two tricarbocyanine 2-deoxyglucosamides (N1R805-2DG and Cypate-2DG), were synthesized in our molecular imaging chemistry laboratory of the Department of Radiology at the University of Pennsylvania. All fluorophores were prepared in-house, except the Cypate (Achilefu, S., et al., *J. Med. Chem.* 45:2003-2015 (2002)), which is a generous gift by Dr. Achilefu of the Washington University Medical School.

Confocal Microscopic Studies 9L glioma cells, obtained from Department of Radiation Oncology at University of Pennsylvania, were cultured in Modified Eagle's Medium (NEM) supplemented with 15% newborn calf serum (NCS), 100 U/ml penicillin-streptomycin. Murine melanoma B16 cells, obtained from Dr. Theo van Berkel's laboratory at the University of Leiden, Netherlands, were cultured in Dulbeco's modified Eagle's medium (DMM) supplemented with 10% fetal bovine serum (FBS) and 100 U/n-d penicillin-streptomycin Cells were grown at 37° C. in an atmosphere of 5% $CO_2$ in a humidified incubator. Cells were grown for 5 days in 4-well Lab-Tek chamber slides (Naperville, Ill.) before the experiment. Indicated amounts of NIRF-2DGs with or without D-Glucose and Rbodarninc-123 were incubated with 9L glioma cells/B16 melanoma cells at 37° C. for 30 min after 3 washes with Dulbecco's Phosphate Buffered Saline (D-PBS). After incubation, the cells were washed five times with ice-cold PBS and Fixed for 20 minutes with 2% formaldehyde in PBS at room temperature. Then the chamber slides were mounted and sealed for confocal niicroscopic analysis. Confocal aticroscopic images were obtained with TCS SPII laser scanning confocal microscope (LSCM) (Heidelber, Germany).

Tumor Bearing Animal Models

Two tumor bearing animal models were used for this study. 9L glioma bearing rat model was obtained by implanting 2×106 Cells in the flank of male Fisher 344 rats (150-200g) via subcutaneous injection. Animals were studied when tumor size reached 2 cm×1.8 cm. To facilitate the in vivo NM imaging using Palomar™ Imager, KB tumor (squamous cell carcinoma) bearing nu/nu mouse model was also used. The average tumor size was 0.8 cm×0.8 cm.

Sample Preparation for Fluorescent Cryo-Imaging

The 9L glioma-bearing rat was anaesthetized intraperitoneally by injecting Ketamine (75 mg/kg) and Xylazine (10 ing/kg) and was given Pyro-2DG (1 mL, concentration: 0.5 mg/ml) via tail vein injection within 2 min. After 2 hirs, the rat was immersed in pre-cooled isopentane (−150° C.) and transferred to liquid nitrogen (−196° C.) 5 minutes later. Tumors and the surrounding muscle tissues were then surgically excised, embedded in a mixture buffer (ethaiiol-glycerol-water, freeze point: −30° C.), and mounted for fluorescent Cryo-imaging.

Fluorescent and redox ratio imaging of tumors with the Cryo-Imager (Quistorff, B., et al., *Analytical Biochemistry* 148:389-400 (1985))

The frozen tumor sample was ground flat and then further ground to obtain images every 100 μm from the top surface to the bottom of the tumor. A bifurcated optical fiber bundle (7 quartz fibers, 70 pi core diameter for each, 0.34 numerical aperture, 1 fiber for emission in center, 6 fibers for excitation around the emission fiber) stepped across the tissue surface at a fixed distance. The excitation filter and the emission filter for detecting the fluorescent signals of each substance were designed based on the absorption and emission spectra of each fluorophores (See FIG. 1). Using a Mercury Arc lamp as the excitation light source, the fluorescent signals of oxidized flavoprotein (Fp, filters: Ex: 44ODF20, Em: 52ODF40), reduced pyridine nucleotide (PN, filters; Ex: 365HT25, Em: 455DF70) were also obtained for each depth of the tumors. The redox ratio of PN/(Fp+PN) and Fp/(FP+PN) calculated with MATLAB represented the reduced state and oxidized state of the mitochondria, respectively. The scanning was performed at 128×128 steps that covered 1,024×1.024 cm$^2$ area (80 μm in-plane resolution).

In vivo real time fluorescent imaging of tumors with the Palomar™ Imager (Benaron, D. A., et al., *Molecular Imaging* 2:S194 (2003))

NIRF805-2DG probe (100 μL of 1 μM) was administered intravenously to the nu/nu mice with KB tumors. A series of real time Palomar™ images were taken at different time points. The Palomar Imager, developed by the Spectros Corp., Calif., is a flexible system designed for imaging the distribution and localization of targeted fluorescent agents in small animals and humans in room light surgical operating room conditions.

Results and Discussion

For this study, we have synthesized a series of NIRF-2DG conjugates by replacing the [$^{18}$F] atom at the 2-position of the FDG with fluorophores based on either tetrapyrrole dyes or cyanine dyes. These imaging agents are pyropheophorbide 2-deoxyglucosamide (Pyro-2DG), two bacteriochlorin 2-deoxyglucosamides (BChlPP-2DG and BChlE6-2DG), dicarbocyanine 2-deoxyglucosamide (NIR664-2DG) and two tricarbocyanine 2-deoxyglucosamides, NIR805-2DG and Cypate-2DG.

In Vitro Fluorescence Studies

Figure 5:
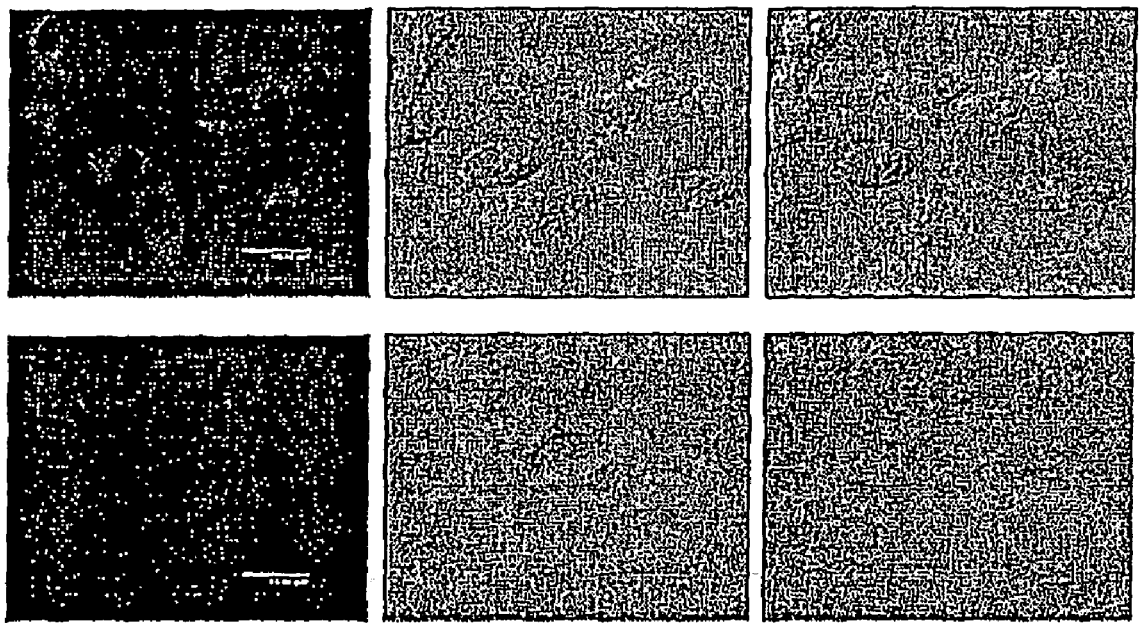
FIG. 5. Confocal images of 9L glioma cells (ex: 630 nm; em: 640-750 nm) incubated with 50 μM Pyro-2DG for 30 min at 37° C. in the absence (upper) and presence (lower) of 50 mM D-glucose. Left column shows the Pyro-2DG fluorescent images, middle column shows the bright field images and the right column shows the overlay images.
Figure 6:
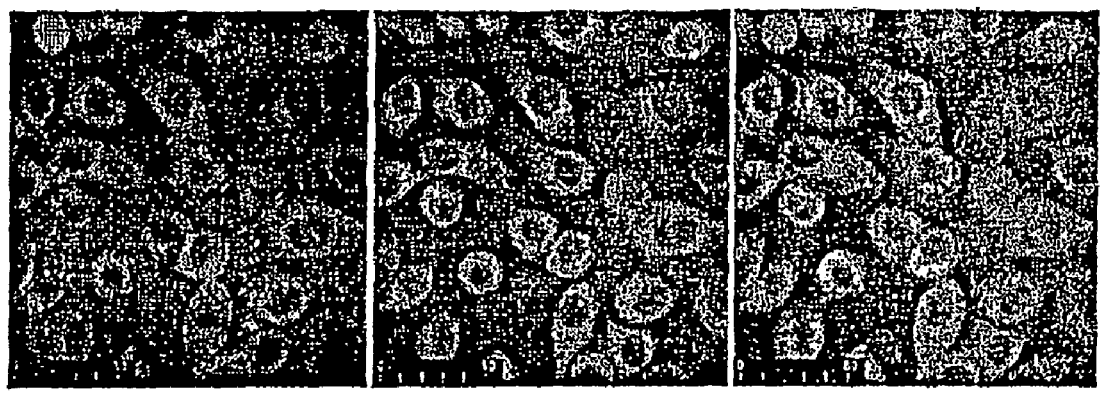
FIG. 6. Comparative intracellular localization of 100 μM Pyro-2DG and 10 μg/ml Rhodamine-123 (mitochondrial probe) in 9L glioma cells at 15 min post-incubation. The overlay picture clearly indicates that both Pyro-2DG and Rhodamine-123 localize in mitochondria.

It is well known that the mechanism of $^{18}$FDG accumulation in tumors is similar to that of native D-glucose since [$^{18}$F] atom of the FDG is very similar to the native 2-OH group of the glucose size wise. To our strategy, the first question needs to be answered is that, will replacement of [$^{18}$F] with a much larger fluorophore moiety affect its GLUT transportation and the subsequent hexokinase mediated phosphorylation reaction? Or using a metaphor, will the "mouse" be able to drag an "elephant" through a mouse hole? To determine whether NIRF-2DG was transported through GLUTs, laser confocal microscopy was first used to demonstrate and quantify the uptake and localization of Pyro-2DG, which has a neutral porphyrin fluorophore, in 9L glioma cells. As shown in FIG. 5, Pyro-2DG localizes within 9L glioma cells at 37° C. and localization was competitively inhibited by D-glucose. In contrast to Pyro-2DG, uptake of pyropheophorbide a in 9L glioma cells is concentration dependent and is not inhibited by D-glucose, indicating that its uptake is GLUT-independent. Thus, Pyro-2DG uptake by 9L glioma cells appears to be through the active-transport mechanism. To farther determine the subcellular localization of Pyro-2DG, we performed the confocal imaging of 9L glioma cells incubated with both Pyro-2DG and Rhodamine 123, a well-known mitochondria tracker. As shown in FIG. 6 below, the results clearly demonstrated that Pyro-2DG localized in mitochondria.

Figure 7:
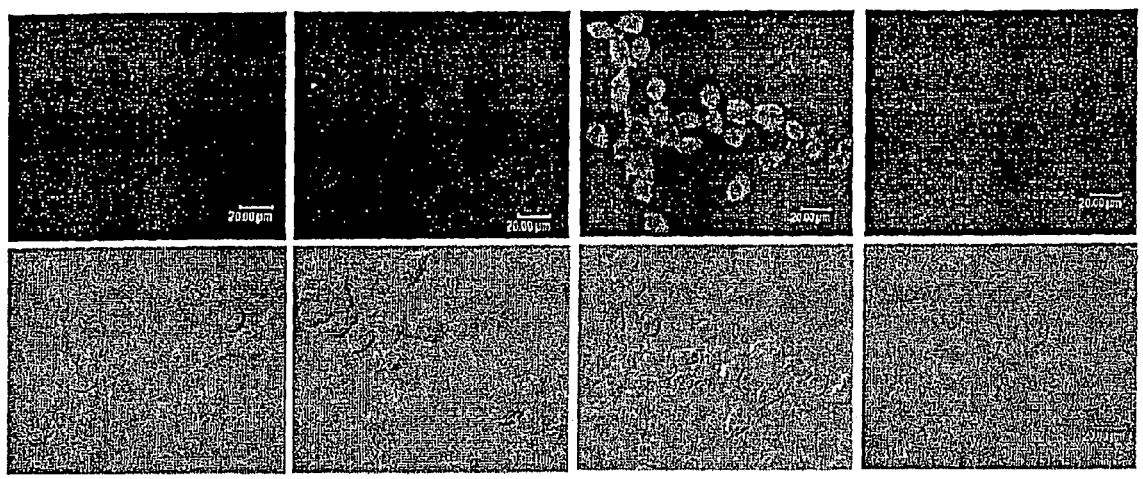
FIG. 7. Confocal images of B16 melanoma cells incubated without NIR664-2DG (first column), with 20 μM NIR664-2DG (second column), 50 μM NIR664-2DG (third column), and 50 μM NIR664-2DG in competition with 25 μM D-glucose (last column), for 20 min at 37° C. Top row shows the fluorescent images and the bottom row shows the corresponding bright field images.

The same question was asked for other 2-deoxyglucose fluorescent probes, and especially those have charged cyanine fluorophores. To examine the effect of structural difference of different fluorophores on the tumor uptake, similar confocal imaging studies were performed for NIR6642DG. FIG. 7 demonstrated that NIR664-2DG localized within B16 melanoma cells, another GLUTs overexpression tumor line, at 37° C. after 20 minutes incubation, and that localization was competitively inhibited by D-glucose. Thus, cyanine dye based NIRF-2DG probes appear to enter the cells via the same uptake mechanism as do the neutral porphyrin-based NIR-2DG probes.

Figure 8:
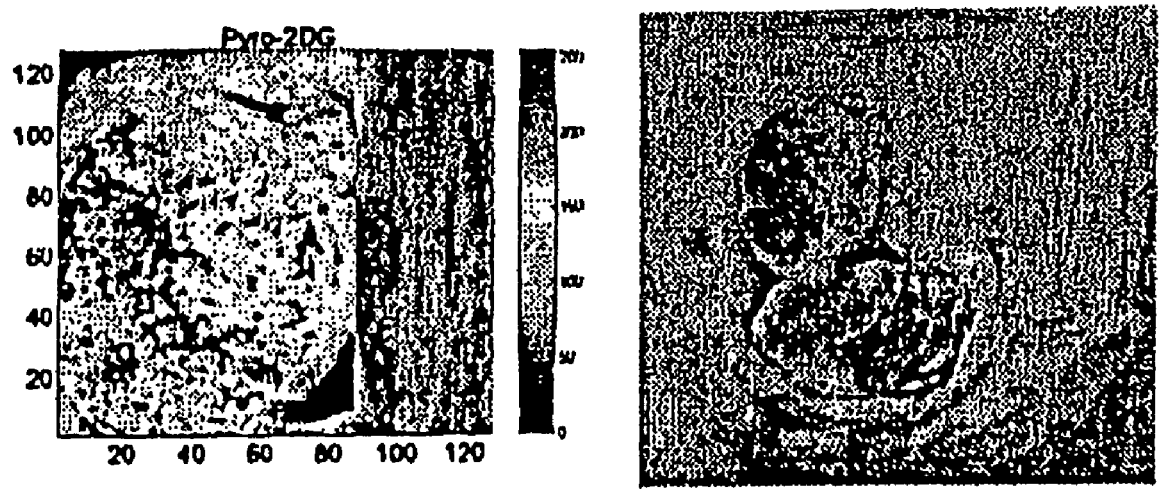
FIG. 8. Tumor versus normal muscle ratio of Pyro-2DG in 9L glioma bearing rats was determined as IO: I calculated from the fluorescence intensity and concentration correlation [x=(y−32.3 75)/10.7292] determined by phantom.

Low temperature fluorescence imaging studies using Cryo-imager. To test these new probes in animal models, surface fluorescence scanning was performed on all probes using a high-resolution low temperature fluorometer (Cryo-imager) and all compounds were found to selectively accumulate in animal tumors. FIG. 8 illustrated that Pyro-2DG accumulated preferentially in the 9L glioma tumors of fasted rats relative to adjacent skeletal muscle at a ratio of 10:1.

Figure 9:
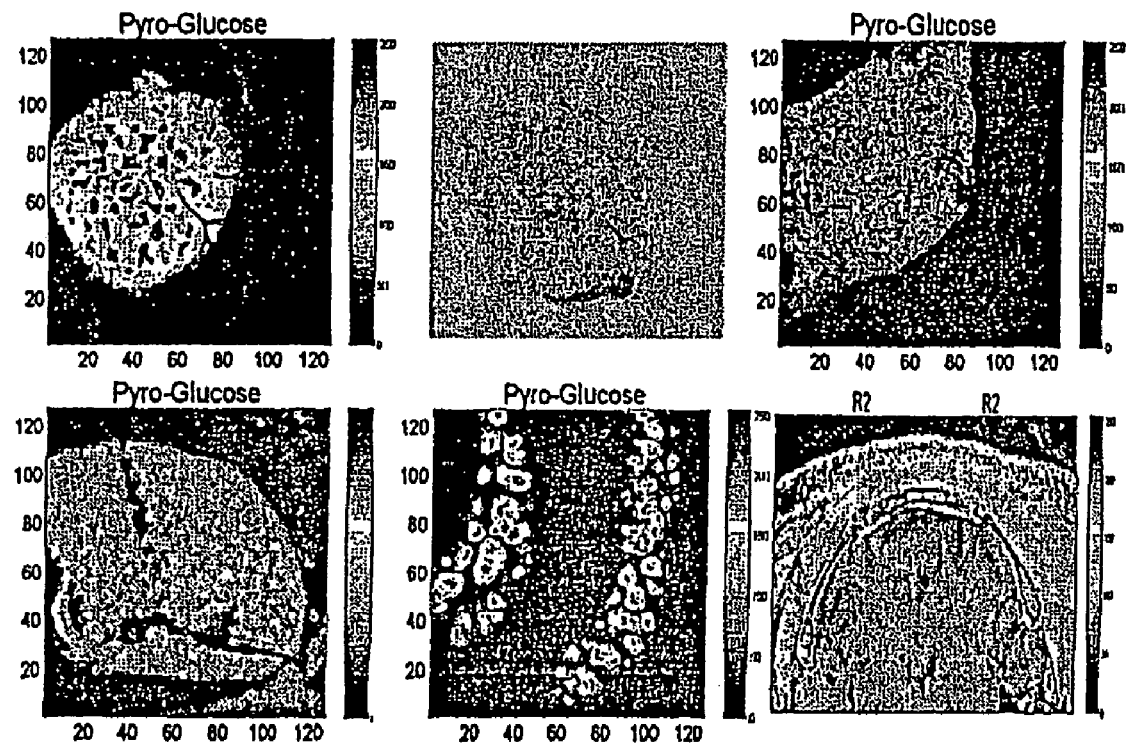
FIG. 9. Pyro-2DG uptake in different organs of a Fisher 344 rat after 1 h tail vein infusion of 2 ml of 2.5 mg/kg Pyro-2DG. Liver (top left), kidney (bottom left), spleen (bottom middle) and brain (bottom right). Images of the frozen liver and of the control liver (no Pyro-2DG), respectively, appear in the top middle and right hand panels.

In order to determine the biodistribution of the Pyro-2DG, a normal Fisher 344 rat was sacrificed and different organs were scanned for Pyro-2DG fluorescence with Cryo-imager 1 hour after Pyro-2DG was intravenously administered. The preliminary results shown in FIG. 9 indicated that Pyro-2DG accumulated predominantly in liver, with lesser accumulation in spleen and kidney, and does not cross the blood-brain barrier.

In vivo real time imaging of tumors with NIRF-2DG.

Figure 10:
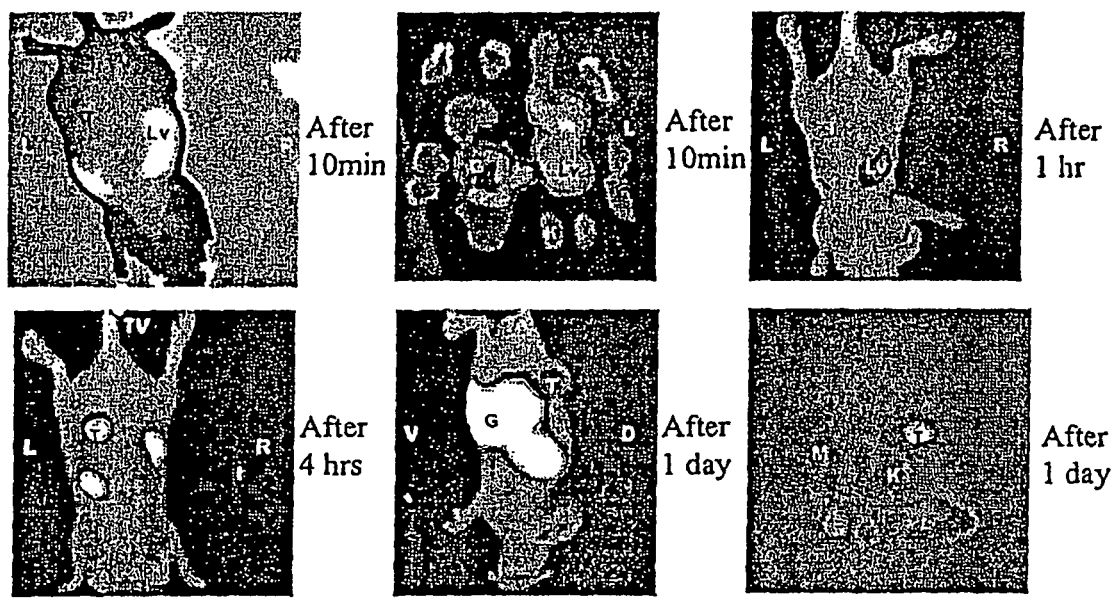
FIG. 10. Real time Palomar images 10 min (top left), 1 hr (top right), 4 hr (bottom left) and 1 day (bottom middle) post-injection with NRF805-2DG. Top middle and bottom right are fluorescent images of all different organs. "T" stands for tumor, "L" stands for liver, "G" stands for gut, "K" stands for kidney, "M" stands for muscle and "S" stands for skin.

An in vivo real time tumor imaging study was performed in bright room light using Spectros' Palomar Optical Contrast system. This is a flexible system designed for imaging the distribution and localization of targeted fluorescent agents in humans and small animals in room light surgical operating room conditions. The images were displayed with 1 second update speed, including all processing/colorization of tumor fluorescence overlaid on a black and white background image. Thus, NIR805-2DG probe (100 μL of 1 AM) was administered intravenously to the nu/nu mice with KB tumors (squamous cell carcinoma) and a series of real time Palomar images were taken at different time points (see FIG. 10). At 10 min post-injection, the fluorescent signal glows everywhere, with a signal forming slightly then strongly over the liver with no localized signal con-Ling from the tumor (T). There is no signal at the tumor, in part due to the scaling of the image (since too much signal everywhere, so scale is raised to see only the liver outline). After 1 hr, the signal is primarily over the liver. By 4 hours, the dorsal tumor glows brightly, and there is less dye signal from the liver. At 1 day, there is a large amount of signal in the gut (G) in the abdomen, but tumor signal still was observed. This study clearly demonstrated that the utility of NIRF-2DG as NIR fluorescent imaging agents for the detection of tumor in vivo.

Conclusion

In conclusion, a series of new NIR fluorescent imaging and PDT agents targeting at the GLUT pathway have been designed and synthesized. Both the in vitro confocal microscopy data and the in vivo imaging studies confirmed that both porphyrin and cyanine dye-based 2-deoxyglucose conjugates are tumor selective. In conjunction with using these new imaging probes, the NIR fluorescence imaging and photodynamic therapy method described earlier provides a prospective high sensitive technology for detecting and treating subsurface cancers at an early stage, thus providing a facial transition between cancer detection and treatment.

Example 3

Experimental Procedures

Materials and General Methods. Melting points are uncorrected. UV-vis spectra were recorded on a Beckman DU-600 or a Perkin-Elmer Lambda spectrophotometer. Fluorescence emission was measured with a Perkin-Elmer LS-50B fluorometer. $^1$H NMR spectra were recorded on a Bruker ASPECT 360 MHz instrument. ESI-MS and HRMS spectrometry analysis were performed at the Mass Spectrometry Facility of the Department of Chemistry, University of Pennsylvania. Methyl pheophorbide a was obtained from *Spirulina pacifica* algae available from Cyanotech Corp., Hawaii. Purpurin-18 methyl ester (1) was synthesized from methyl pheophorbide according to a literature procedure. (Zheng, G.; Li, H.; Zhang, M.; Lund-Katz, S.; Chance, B.; Glickson, J. D., Low-density lipoprotein reconstituted by pyropheophorbide cholesteryl oleate as target-specific photosensitizer. *Bioconjugate Chemistry* 2002, 13, (3), 392-396.) Bacteriochlorophyll a (BChl) was extracted from *R. Sphaeroides* biomass purchased from Frontier Science, Utah. Bacteriopurpurin-18 methyl ester (6) and bacteriopheophorbide a methyl ester (11) were synthesized from BChl according to previously described procedures. (Kozyrev, A. N.; Zheng, G.; Zhu, C. F.; Dougherty, T. J.; Smith, K. M.; Pandey, R. K., Syntheses of stable bacteriochlorophyll-a derivatives as potential photosensitizers for photodynamic therapy. *Tetrahedron Letters* 1996, 37, (36), 6431-6434; Hartwich, G.; Fiedor, L.; Simonin, I.; Cmiel, E.; Schafer, W.; Noy, D.; Scherz, A.; Scheer, H., Metal-substituted bacteriochlorophylls. 1. Preparation and influence of metal and coordination on spectra. *Journal of the American Chemical Society* 1998, 120, (15), 3675-3683). Other chemicals were purchased from Aldrich. Where necessary, solvents were dried before use. For TLC, EM Science TLC plates (silica gel 60 $F_{254}$) were used. Purity of the final conjugates was validated by reverse phase HPLC using a Waters Delta-600 analytical/semi-preparation system equipped with photodiode array and fluorescence detectors.

Purpurin-18-N-3'-(BOC-amino)propylimide, PP18-BOC (2): Purpurin-18 methyl ester (1) (200 mg, 0.346 mmol) and tert-Butyl N-(3-aminopropyl)-carbamate (380 mg, 2.18 mmol) were dissolved in 15 mL benzene. The mixture was refluxed at 78° C. under argon atmosphere for 48 hrs. After removing solvent, the crude residue was purified by silica gel column chromatography with 5% MeOH in $CH_2Cl_2$. The desired product was obtained in 75% yield (190 mg). UV-vis in $CH_2Cl_2$ $\lambda_{max}$: 367 nm (e: $5.3 \times 10^4$), 419 ($1.3 \times 10^5$), 550 ($2.2 \times 10^4$), 662 ($9.4 \times 10^3$) and 706 ($4.1 \times 10^4$). Mass calculated for $C_{42}H_{50}N_6O_6$: 734.4; found by ESI-MS; 757.8 $(M+Na)^+$. $^1$H NMR ($CDCl_3$, δ ppm): 9.27, 9.07 and 8.55 (each, s, 1H, for 10, 5 and 20-H), 7.75 (dd, 1H), 6.17 (d, 1H), 6.06 (d, 1H), 5.72 (brs, 1H), 5.38 (d, 1H), 4.59 (t, 2H), 4.38 (m, 1H), 3.65 and 3.63 (each, s, 3H), 3.37 (m, 4H), 3.29 and 2.94 (each, s, 3H), 2.86 (m, 1H), 2.46 (m, 2H, 1H), 2.21 (m, 2H), 2.00 (m, 1H), 1.80 (d, 3H), 1.54 (s, 12H), −0.2 and −0.31 (each brs, 1H, 2×NH).

Purpurin-18-N-3'-(isothiocyanate)propylimide, PP18-NCS (4): Purpurin-18-N-3'-(BOC-amino)propylimide (190 mg, 0.259 mmol) was dissolved in 3 mL TFA. The mixture was subsequently stirred at room temperature under argon atmosphere. One hour later, TFA was removed by vacuum. The crude residue was diluted with 40 mL $CH_2Cl_2$, and then washed with 30 mL $NaHCO_3$ and 2×30 mL water. The organic layer was dried over anhydrous $Na_2SO_4$. After removing solvent, purpurin-18-N-3'-(amino)propylimide (3) was obtained in 140 mg (yield 86%). It was then used directly for the next reaction without further purification. This intermediate (140 mg, 0.22 mmol) and 1,1'-thiocarbonyldiimidazole (43 mg, 0.243 mmol) were dissolved in 10 mL $CH_2Cl_2$. The reaction mixture was refluxed at 40° C. under argon atmosphere for 3 hrs. After removing solvent, the crude obtained was purified by silica gel plate with 2% MeOH in $CH_2Cl_2$. The desired isothiocyanate product was obtained in 75% yield (110 mg). UV-vis in $CH_2Cl_2$ $\lambda_{max}$: 367 nm (ϵ: $4.8 \times 10^4$), 418 ($1.5 \times 10^5$), 550 ($1.0 \times 10^4$), 649 ($2.4 \times 10^3$) and 706 ($5.5 \times 10^4$). Mass calculated for $C_{38}H_{40}N_6O_4S$: 699.2729 $(M+Na)^+$; found by HRMS: 699.2691 $(M+Na)^+$. $^1$H NMR ($CDCl_3$, δ ppm): 9.56, 9.32 and 8.56 (each s, 1H, for 10, 5 and 20-H), 7.87 (dd, 1H), 6.27 (d, 1H), 6.15 (d, 1H), 5.31 (d, 1H), 4.60 (t, 2H), 4.35 (m, 1H), 3.87 (t, 2H), 3.85 (s, 3H), 3.65-3.55 (m, 5H,), 3.34 and 3.13 (each s, 3H), 2.75 (m, 1H), 2.40 (m, 4H), 1.97 (m, 1H), 1.76 (d, 3H), 1.65 (t, 3H), 0.08 (m, 2H, 2 X NH).

Preparation of 2-deoxyglucose conjugate of Purpurin-18-N-3'-(isothiocyanate)propylimide, PP18-2DG (5): D-Glucosamine hydrochloride (13 mg, 0.06 mmol) was added to a solution containing sodium methoxide (3.24 mg, 0.06 mmol) in 3 mL DMSO. The reaction mixture was stirred at room temperature for 2 hrs, and purpurin-18-N-3'-(isothiocyanate) propylimide (19 mg, 0.028 mmol) and 50 μL diisopropylethylamine were added. The resulting solution was stirred under argon atmosphere for 20 hrs. After removing solvent and base by vacuum, the crude obtained was washed with both $CH_2Cl_2$ and, water and subsequently crystallized from MeOH. The desired 2-deoxyglucose conjugate (5) was obtained (8 mg). The filtrate was further concentrated and purified by silica gel plate chromatography (10% MeOH in $CH_2Cl_2$) to yield 4 mg of product. Thus, the total yield for 5 was 50% (12 mg). UV-vis in DMSO $\lambda_{max}$: 366 nm (ϵ: $5.3 \times 10^5$), 419 ($1.4 \times 10^4$), 550 ($2.4 \times 10^4$), 648 ($8.0 \times 10^3$) and 705 ($5.2 \times 10^4$). Mass calcd for $C_{44}H_{53}N_7O_9S$: 878.3523 $(M+Na)^+$; found by HRMS; 878.3542 $(M+Na)^+$. $^1$H NMR (DMSO-d-6, δ ppm): 9.27, 9.16 and 8.85 (each s, 1H, for 10, 5 and 20-H), 8.01 (dd, 1H), 7.80 (br, 1H), 6.55 (br, 1H), 6.33 (d, 1H), 6.12 (d, 1H), 5.24-4.21 (9H), 3.80-3.40 (13H), 2.90 (s, 3H), 2.60 (m, 1H), 2.50-2.30 (m, 2H), 2.08 (m, 2H), 1.8 (m, 1H), 1.72 (d, 3H), 1.41 (t, 3H), −0.61 and −0.67 (each s, 1H, 2×NH).

Bacteriopurpurin-18-N-3'-(BOC-amino)propylimide, BChlPP-BOC (7): Bacteriopurpurin-18 methyl ester (6) (100 mg, 0.186 mmol) and tert-Butyl N-(3-aminopropyl)-carbamate (250 mg, 1.44 mmol) were dissolved in benzene (7 mL). The solution was refluxed at 78° C. under argon atmosphere for 48 hrs. After removing solvent, the residue so obtained was purified by silica gel column chromatography with 5% MeOH in $CH_2Cl_2$ to afford the title compound in 18% yield (24 mg). UV-vis in $CH_2Cl_2$ $\lambda_{max}$: 364 nm ($\epsilon$: $8.4\times10^4$), 414 ($4.2\times10^4$), 544 ($3.1\times10^4$), 739 ($7.6\times10^3$) and 820 ($6.3\times10^4$). Mass calcd for $C_{42}H_{52}N_6O_7$: 752.4 ($M^+$); found by ESI-MS: 775.8 $(M+Na)^+$.

$^1$H NMR ($CDCl_3$, $\delta$ ppm): 9.23, 8.80 and 8.62 (each s, 1H, for 5, 10 and 20-H), 5.62 (br, 1H, -NHBoc), 5.24 (m, 1H), 4.52 (m, 2H), 4.28 (m, 2H), 4.09 (m, 1H), 3.69, 3.59, 3.54 and 3.17 (each s, 3H), 3.31 (m, 2H), 2.71 (m, 1H), 2.37 (m, 3H), 2.15 (m, 21), 2.10-1.90 (m, 2H), 1.81 (d, 3H), 1.72 (d, 3H), 1.50 (s, 9H), 1.11 (t, 3H), −0.46 and −0.68 (each s, 1H 2×NH).

Bacteriopurpurin-18-N-3'-(amino)propylimide, BChlPP-$NH_2$ (8): The BOC derivative of bacteriopurpurinimide (24 mg, 0.032 mmol) was dissolved in TFA (2 mL). The solution was stirred at room temperature under argon atmosphere for 1 hr. After removing TFA by vacuum, the residue was redissolved in $CH_2Cl_2$ (40 mL), and washed with $NaHCO_3$ (20 mL) and water (2×30 mL). The organic layer was dried over anhydrous $Na_2SO_4$. Removing solvent generated the title compound in 86% yield (18 mg). UV-vis in $CH_2Cl_2$ $\lambda_{max}$: 365 nm ($\epsilon$: $8.7\times10^4$), 416 ($5.6\times10^4$), 547 ($3.4\times10^4$), 736 ($9.5\times10^3$) and 822 ($6.5\times10^4$). Mass calculated for $C_{37}H_{44}N_6O_5$: 652.3; found by ESI-MS; 675.3 $(M+Na)^+$. $^1$H NMR ($CDCl_3$, $\delta$ ppm): 9.23, 8.80 and 8.63 (each s, 1H, 5-H; 10-H and 20-H), 5.27 (m, 1H), 4.54 (m, 2H), 4.28 (m, 2H), 4.09 (m, 1H), 3.69, 3.58, 3.55 and 3.17 (each s, 3H), 2.95 (m, 2H), 2.69 (m, 1H), 2.33 (m, 4H), 2.10-1.90 (m, 3H), 1.80 (d, 3H), 1.72 (d, 3H), 1.10 (t, 3H), −0.49 and −0.71 (each s, 1H, 2×NH).

Bacteriopurpurin-18-N-3'-(isothiocyanate)propylimide, BChlPP-NCS (9): Amino derivatives of bacteriopurpurinimide (18 mg, 0.027 mmol) and 1,1'-thiocarbonyldiimidazole (5.3 mg, 0.0298 mmol) were dissolved in $CH_2Cl_2$ (2 mL). The solution was stirred at room temperature under argon atmosphere for 20 hrs. After removing solvent, the residue was purified by silica gel plate chromatography with 2% MeOH in $CH_2Cl_2$ to obtain the desired product in 75% yield (14 mg). UV-vis in $CH_2Cl_2$ $\lambda_{max}$: 365 nm ($\epsilon$: $8.4\times10^4$), 416 ($4.8\times10^4$), 547 ($3.5\times10^4$), 736 ($9.0\times10^3$) and 822($6.3\times10^4$). Mass calculated for $C_{38}H_{12}N_6O_5SNa$: 117.2835; found by HRMS; 717.2823 $(M+Na^+)$. $^1$H NMR ($CDCl_3$, $\delta$ ppm): 9.23, 8.80 and 8.63 (each s, 1H, for 5, 10 and 20-H), 5.24 (d, 1H), 4.60 (t, 2H), 4.29 (m, 2H), 4.09 (m, 1H, 18-H), 3.85 (t, 2H), 3.69, 3.58, 3.55 and 3.17 (each s, 3H), 2.71 (m, 1H), 2.40 (m, 5H), 2.06 (m, 2H), 1.81 (d, 3H), 1.72 (d, 3H), 1.11 (t, 3H), −0.44 and −0.67 (each s, 1H,2×NH).

Preparation of 2-deoxyglucose conjugate of Bacteriopurpurin-18-N-3'-(isothiocyanate)-propylimide, BChlPP-2DG (10): D-Glucosamine hydrochloride (10 mg, 0.046 mmol) was added to a solution of sodium methoxide (2.5 mg, 0.046 mmol) in DMSO (2 mL). After stirring for 2 hrs, isothiocyanate containing bacteriopurpurinimide (16 mg, 0.023 mmol) and diisopropylethylamnine (30 µL) were added and allowed to react for 18 h to form the conjugate. After removing the solvent, the crude so obtained was purified by silica gel plate chromatography with 20% MeOH in $CH_2Cl_2$. The desired conjugate (10) was obtained in 15% yield (3 mg). UV-vis in DMSO $\lambda_{max}$: 365 nm ($\epsilon$: $8.4\times10^4$), 416 ($7.5\times10^4$), 550 ($2.9\times10^4$), 728 ($2.5\times10^4$) and 821 ($3.2\times10^4$). Mass calcd for $C_{44}H_{53}N_7O_9S$: 896.3629$(M+Na)^+$; found by HRMS; 896.3671 $(M+Na)^+$.

Bacteriochlorin $e_6$-13-carboxy-N-3'-(BOC-amino)propylamide, BChlE6-BOC (12): Bacteriopheophorbide a methyl ester, 11 (625 mg, 1 mmol) was dissolved in chloroform (50 mL) and tert-butyl N-(-3-aminopropyl)-carbamate (380 mg, 2.18 mmol) was dissolved in 15 mL benzene. The mixture was refluxed at 78° C. under argon atmosphere for 48 h. After removing solvent, the crude residue was purified by silica gel column chromatography with 5% acetone in dichloromethane. The desired product was obtained in 70% yield (561 mg), UV-vis in $CH_2Cl_2$ $\lambda_{max}$: 358 nm ($\epsilon$: $2.23\times10^4$), 520 ($0.5\times10^4$), 754 ($1.98\times10^4$), Emission $\lambda_{max}$ ($CH_2Cl_2$): 758 nm, Mass. calcd for $C_{39}H_{50}N_6O_6$ 798.43 found by ESI-MS; 799.43 $(M+1)^+$ $^1$H NMR ($CDC_3$, $\delta$ ppm) 9.33, 8.71 and 8.58 (each, s, 1H, for 5, 10, 20-H), 6.96 (s, 1H, ), 4.33 (m, 2H), 4.05(m, 2H), 3.87 (s, 3H), 3.63 (s, 3H), 3.50 (s, 3H), 3.46 (s, 3H), 3.17 (s, 3H), 2.54 (m, 2H), 2.25-2.09(m, 4H), 1.82 (d, 3H), 1.79 (d, 3H),1.14 (t, 3H), 0.49 and 0.10 (each, s, 2×qjNH).), $^{13}$C NMR ($CDCl_3$) 198.83, 173.71, 169.62, 168.34, 169.77, 169.75, 163.86, 158.12, 148.29, 139.27, 138.51, 137.03, 136.51, 133.46, 128.83, 121.54, 108.20, 99.83, 97.86, 96.00, 64.55, 55.14, 53.01, 51.89, 50.79, 49.90, 49.06, 33.53, 31.14, 30.37, 30.12, 29.49, 29.45, 28.54, 23.85, 23.38, 13.92, 12.01, 11.01.

Bacteriochlorin $e_6$-13-carboxy-N-3'-(amino)propylamide (BChlE6-$NH_2$, 13) and Bacteriochlorin $e_6$-13-carboxy-N-3'-(isothiocyanate)propylamide (BChlE6-NCS, 14): BChlE6-BOC (400 mg, 0.5 mmol) was dissolved in 6 mL TFA. The mixture was stirred at room temperature under argon atmosphere. One hour later, TFA was removed by vacuum. The crude residue was diluted with 40 mL $CH_2Cl_2$, washed once with 30 mL $NaHCO_3$ and twice with 30 mL water after which the organic layer was dried over anhydrous $Na_2SO_4$. After removing solvent, BChlE6-$NH_2$ was obtained (300 mg, 0.43 mmol) at an 86% yield. UV-vis in $CH_2Cl_2$ $\lambda_{max}$: 358 nm ($\epsilon$: $2.23\times10^4$), 520 ($0.5\times10^4$), 752 ($1.98\times10^4$), Emission $\lambda_{max}$ ($CH_2Cl_2$): 770 nm, Mass. calculated for $C_{39}H_{50}N_6O_6$ 698.38 found by ESI-MS; 698.26.

BChlE6-$NH_2$ was then used directly for the next reaction step without further purification. BChl-$NH_2$ (300 mg, 0.43 mmol) and 1.1'-thiocarbonyldiimidazole (71.3 mg) were dissolved in 20 mL $CH_2Cl_2$. The reaction mixture was subsequently refluxed at 40° C. under argon atmosphere for 3 h, and the solvent was removed. The residue was purified by silica gel chromatography with 2% MeOH—$CH_2Cl$, and 95 mg of BChlE6-NCS was collected (yield 75%). UV-vis in $CH_2Cl_2$ $\lambda_{max}$: 358 nm ($\epsilon$: $2.23\times10^4$), 520 ($0.5\times10^4$), 754 ($1.98\times10^4$), Emission $\lambda_{max}$ ($CH_2Cl_2$): 758 nm, Mass. calcd for $C_{39}H_{50}N_6O_6$ 798.43 found by ESI-MS; 799.43 $(M+1)^+$ $^1$H NMR ($CDCl_3$, $\delta$ ppm) 8.99, 8.50 and 8.43 (each, s, 1H, for 10, 5 and 20-H), 6.10 (s, 1H, ), 4.33 (m, 2H), 4.05(m, 2H), 3.87 (s, 3H), 3.63 (s, 3H), 3.50 (s, 3H), 3.46 (s, 3H) 3.17 (s, 3H), 2.54 (m, 2H), 2.25-2.09(m, 4H), 1.82 (d, 3H), 1.79 (d, 3H),1.14 (t, 3H), −0.44 and −0.67 (each, s, 2×NH).), $^{13}$C NMR ($CDCl_3$, $\delta$ ppm) 198.83, 173.71, 169.62, 168.34, 169.77, 169.75, 163.86, 158.12, 148.29, 139.27, 138.51, 137.03, 136.51, 133.46, 128.83, 121.54, 104.37, 98.51, 97.63, 96.78, 57.48, 53.24, 52.45, 51.84, 48.23, 46.98, 43.21, 37.97, 37.88, 33.39, 31.23, 30.22, 30.13, 29.50, 23.80, 23.34, 13.91, 12.01, 11.01.

Preparation of 2-deoxyglucose conjugate of bacteriochlorin $e_6$-isothiocyanate, BChlE6-2DG (15): D-Glucosamine hydrochloride (23.5 mg, 0.11 mmol) was added to a solution of sodium methoxide (5.9 mg, 0.11 mmol) in DMF (5 mL). After stirring for 2 h, BChlE6-NCS (40 mg, 0.054 mmol) and N,N-diisopropylethylamine (71 µL) were added and allowed to react for 18 h to from the conjugate. After removing the solvent, the crude obtained was purified by silica gel plate chromatography with 20% MeOH in $CH_2Cl_2$. The desired conjugate was obtained in 60% yield (30 mg). Uv-vis in MeOH $\lambda_{max}$: 358 nm ($\epsilon$: 2.23×10$^4$), 520 (0.5×10$^4$), 754 (1.98×10$^4$), Emission $\lambda_{max}$ (MeOH): 768 nm, Mass. calcd for C$_{45}$H$_{59}$N$_7$O$_{11}$S+Na: 942.4047, found by high resolution MS: 942.4081 (<5 ppm). $^1$H NMR (CDCl$_3$, $\delta$ ppm) 9.24, 8.74 and 8.61 (each, s, 1H, for 10, 5, 20-H), 5.34 (d, 1H), 5.11 (d, 1H), 4.31 (m, 1H), 4.26(m, 1H), 4.17 (m, 2H), 4.03 (brs. 8H), 3.87 (m, 4H), 3.74 (m, 2H), 3.72 (s, 3H), 3.58 (s, 3H) 3.57 (s, 3H), 3.34 (s, 3H), 3.18 (s, 3H), 2.58 (m, 2H), 2.40-2.03(m, 8H), 1.82 (d, 3H), 1.79 (m, 2H), 1.59 (d, 3H),1.05 (t, 3H), −0.61 and −0.67 (each s, 1H, 2×NH), $^{13}$C NMR (CDCl$_3$) 198.83 (3° C.), 173.71 (17$^3$ C), 169.62 (15$^2$ C), 168.34 (13$^1$ C), 169.77 (1 C), 169.75 (133 C), 163.86 (4 C), 158.12 (14 C), 148.29 (16 C), 139.27 (11 C), 138.51(6 C), 137.03 (9 C), 136.51 (12 C), 133.46 (13 C), 128.83 (3 C), 121.54 (2 C), 108.20 (15 C), 99.83 (5 C), 97.86 (10 C), 96.00 (20 C), 64.55 (132 C), 55.14 (8 C), 53.01 (13$^4$ C), 51.89 (17$^4$ C), 50.79 (17 C), 49.90 (18 C), 49.06 (7 C), 33.53 (3$^2$ C), 31.14 (17$^2$ C), 30.37 (8$^1$ C), 30.12 (17$^1$ C), 28.54 (13$^7$, 13$^8$, 13$^9$ C, 3C) 23.85 (7$^1$ C), 23.38 (18$^1$ C), 13.92 (2 $^1$ C), 12.01 (12 $^1$ C), 11.01 (8$^2$ C). HPLC retention time 30.1 min (using 0.1M TEAA and CH$_3$CN as BPLC eluent, from 10% CH$_3$CN to 90% CH$_3$CN for 45 min).

In vivo NIR optical imaging system: To image and localize subsurface fluorochrome labeled tumors, an NLR imaging system utilizing diffusion photons (Patterson, M. S.; Chance, B.; Wilson, B. C., Time resolved reflectance and transmittance for the non-invasive measurement of tissue optical properties. *Applied Optics* 1989, 28, 2331-2336.

Fishkin, J. B.; Gratton, E., Propagation of photon-density waves in strongly scattering media containing an absorbing seni-infinite plane bounded by a straight edge. *Journal of the Optical Society of America A* 1993, 10, 127-140.) has been developed. The in vivo fluorescence optical imaging system consists of a pair of laser diodes operating at 780 nm. The light intensities are modulated by 50 MHz sinusoidal radio frequency waves, but with a 180° phase difference between them. Detection sensitivity and localization accuracy are enhanced through phase cancellation techniques. (Chance, B.; Kang, K.; He, L.; Weng, J.; Sevick-Muraca, E. M., Highly sensitive object location in tissue models with linear in-phase and anti-phase multi-element optical arrays in one and two dimensions. *Proceedings of the National Academy of Sciences USA* 1993, 90, 3423-3427.

Chance, B.; Kang, K.; He, L.; Liu, H.; Zhou, S., Precision localization of hidden absorbers in body tissues with phased-array optical systems. *Review of Scientific Instruments* 1996, 67, 4324-4332.

Intes, X.; Chen, Y.; Li, X. D.; Chance, B., Detection limit enhancement of fluorescent heterogeneities in turbid media by dual-interfering excitation. *Applied Optics* 2002, 41, (19), 3999-4007.) The excitation photons are delivered to the imaging chamber filled with highly scattering medium (Intralipid® and ink) through fiber optics. The tumor-bearing animal injected with BChlPP-2DG is immersed inside the imaging chamber, and the tumor is placed within 1.5 cm from the outside surface. A 3-mm-in-diameter fiber bundle collects the fluorescence signal from the fluorophore taken by in the tumor. An interference filter at 830 nm is used to select the emitted fluorescent photons. The fluorescence signal is then detected by the photomultiplier tube (PMT) and demodulated by the 50 MD receiver to obtain the amplitude and phase information. The imaging probe consists of two source fibers with a separation of 2 cm and a detection fiber bundle with equal distance (4 cm) from each source. The source and detector fibers can be scanned in tandem under the control of a stepper motor. After finishing one axial scan, the probe can be rotated to another angle to perform another axial scan. Multiple radial scans in different directions can be acquired for object localization. (Chen, Y.; Mu, C. P.; Intes, X.; Blessington, D.; Chance, B., Near-infrared phase cancellation instrument for fast and accurate localization of fluorescent heterogeneity. *Review of Scientific Instruments* 2003, 74, (7), 3466-3473.) The optical imaging probe is placed on the surface of the imaging chamber and scanned through a 5-cm-in-diameter area for subsurface localization of fluorescence enhanced tumor. Two-dimensional localization of the subsurface fluorochrome is obtained by fitting the experimental data to the analytical solutions and searching for the minimum of the probability function $\chi^2$. (Chen, Y.; Zheng, G.; Zhang, Z. H.; Blessington, D.; Zhang, M.; Li, H.; Iiu, Q.; Zhou, L.; Intes, X.; Achilefu, S.; Chance, B., Metabolism-enhanced tumor localization by fluorescence imaging: in vivo animal studies. *Optics Letters* 2003, 28, (21), 2070-2072).

Results and Discussion

In order to effectively functionalize bacteriochlorophylls utilized to label biomolecules, the reactive functional groups that are added should not only be stable enough for prolonged storage ability but should also exhibit high labeling efficiencies with minimal side reactions; ultimately, they must produce a stable covalent bond. Isothiocyanate has been widely used for coupling with primary and secondary amines of biologically important molecules; (Flanagan, J. H.; Khan, S. H.; Menchen, S.; Soper, S. A.; Hammer, R. P., Functionalized tricarbocyanine dyes as near-infrared fluorescent probes for biomolecules. *Bioconjugate Chemistry* 1997, 8, (5), 751-756.) thus, it became the labeling functionality of choice. Pandey et al. have shown that unstable bacteriochlorophyll a analogs containing a five-member isocyclic ring can be converted to the related bacteriochlorin bearing either a fused six-member anhydride or imide ring systems; these derivatives are referred to as bacteriopurpurin-18 (BCHlPP) and bacteriopuwpurinimide analogs, respectively. (Kozyrev, A. N.; Zheng, G.; Zhu, C. F.; Dougherty, T. J.; Smith, K. M.; Pandey, R. K., Syntheses of stable bacteriochlorophyll-a derivatives as potential photosensitizers for photodynamic therapy. *Tetrahedron Letters* 1996, 37, (36), 6431-6434.) The latter is particularly interesting because it presents a unique opportunity to introduce the isothiocyanate labeling functionality at the fused imide ring for convenient conjugation to tumor-homing molecules. To develop an effective synthetic strategy, model studies were performed by using a less expensive substrate, purpurin-18 methyl ester, 1 (Zheng, G.; Potter, W. R.; Camacho, S. H.; Missert, J. R.; Wang, G. S.; Bellnier, D. A.; Henderson, B. W.; Rodgers, M. A. J.; Dougherty, T. J.; Pandey, R. K., Synthesis, photophysical properties, tumor uptake, and preliminary in vivo photosensitizing efficacy of a homologous series of 3-(1'-alkyloxy) ethyl-3-devinaylpurpurin-18-N- alkylimides with variable lipophilicity. *Journal of Medicinal Chemistry* 2001, 44, (10), 1540-1559.). As shown in Scheme 1, reaction of 1 with tert-butyl N-(3-aminopropyl)-carbamate at reflux temperature gave the corresponding BOC-protected amino containing purpurinimide (PP-BOC, 2) in high yield. Upon TFA cleavage of the BOC protecting group, purpurin-18-N-3'-(amino)propylimide, 3, was obtained. The amino functionality in 3 was further converted to the desired isothiocyanate labeling moiety in compound 4 by reacting with 1,1'-thiocarbonyldiimidazole. The overall yield of this three-step process was about 50%. To test the utility of this functionalized model compound, a 2-deoxyglucose moiety was selected as the tumor-homing molecule via the glucose transporter (GLUT) pathway. (Zhang, M.; Zhang, Z. H.; Blessington, D.; Li, H.; Busch, T. M.; Madrak, V.; Miles, J.; Chance, B.; Glickson, J. D.; Zheng, G., Pyropheophorbide 2-deoxyglucosamide: A new photosensitizer targeting glucose transporters. *Bioconjugate Chemistry* 2003, 14, (4), 709-714.) Thus, following a procedure we reported earlier, (Zhang, M.; Zhang, Z. H.; Blessington, D.; Li, H.; Busch, T. M.; Madrak, V.; Miles, J.; Chance, B.; Glickson, J. D.; Zheng, G., Pyropheophorbide 2-deoxyglucosamide: A new photosensitizer targeting glucose transporters. *Bioconjugate Chemistry* 2003, 14, (4), 709-714) isothiocyanate containing purpurin-18 was reacted with D-glucosamine to yield the desired conjugate 5 in 50% yield.

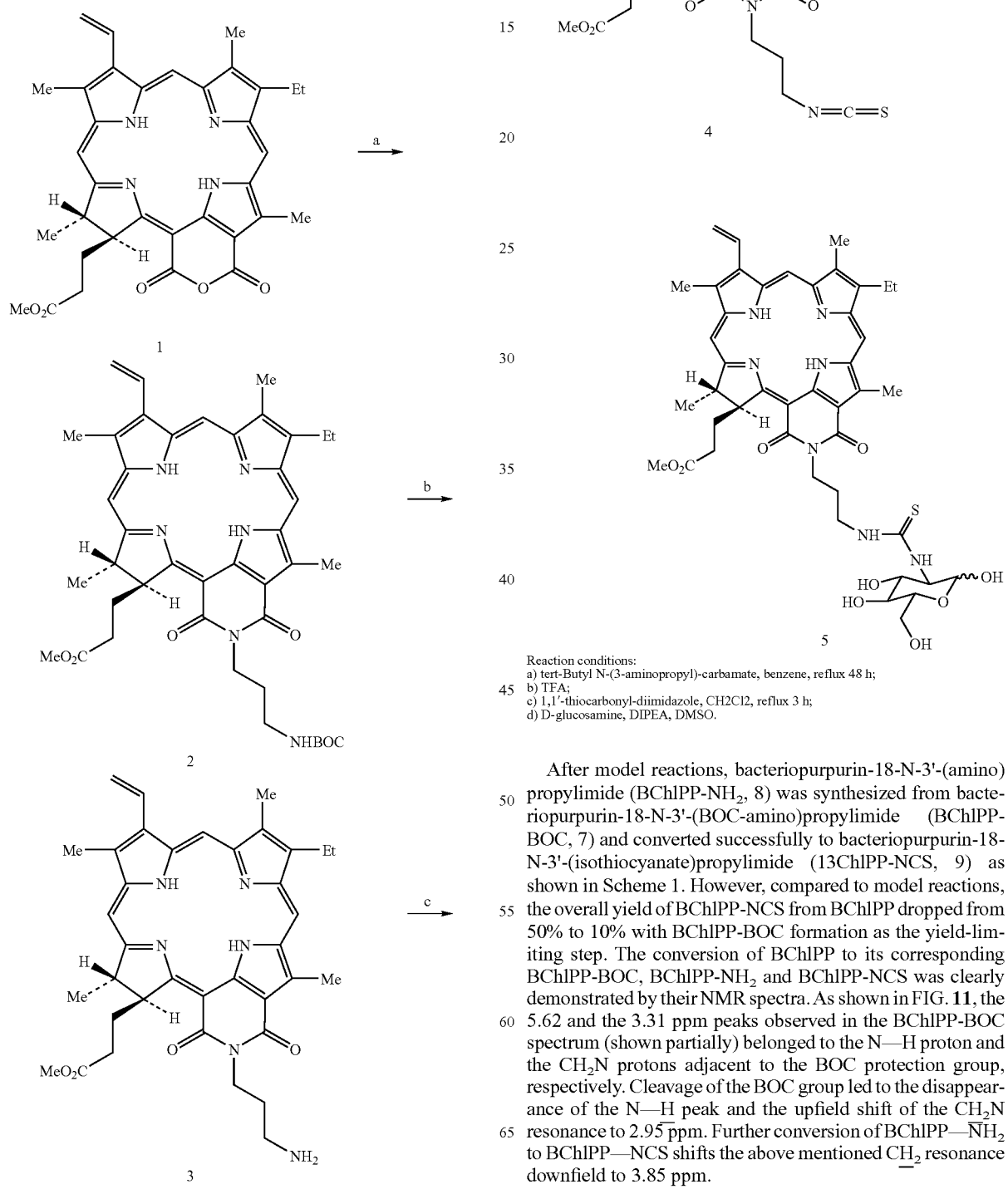

Scheme 1.
Synthesis of an isothiocyanate-containing purpurin-18 and its conversion to its corresponding 2-deoxyglucose conjugate.

Reaction conditions:
a) tert-Butyl N-(3-aminopropyl)-carbamate, benzene, reflux 48 h;
b) TFA;
c) 1,1′-thiocarbonyl-diimidazole, CH2Cl2, reflux 3 h;
d) D-glucosamine, DIPEA, DMSO.

Figure 11:
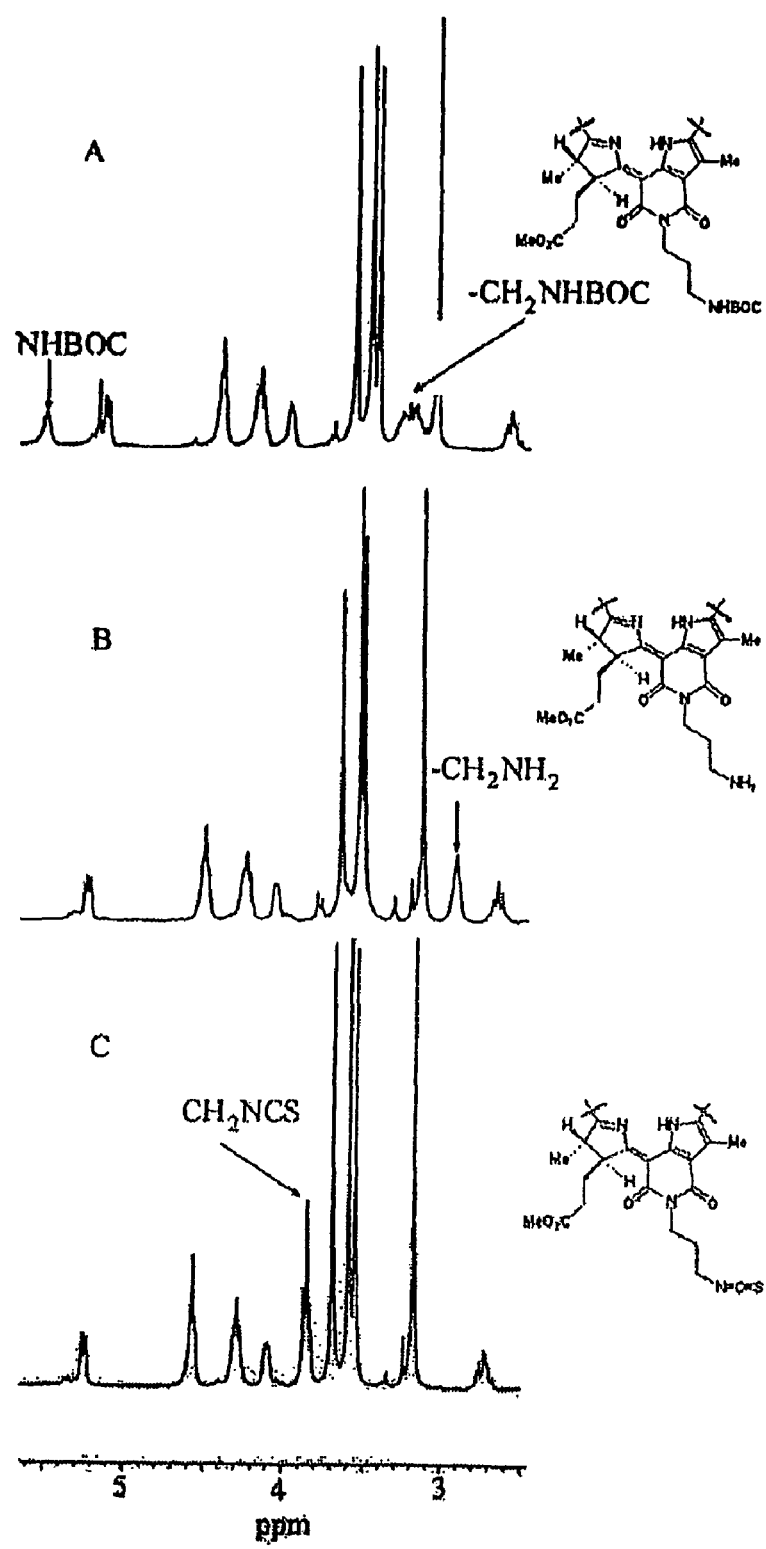
FIG. 11. Chemical shifts of $CH_2NHBOC$, $CH_2NH_2$ and $CH_2NCS$ in $^1H$ NMR spectra of functionalized bacteriochlorophylls.

After model reactions, bacteriopurpurin-18-N-3′-(amino)propylimide (BChlPP-NH$_2$, 8) was synthesized from bacteriopurpurin-18-N-3′-(BOC-amino)propylimide (BChlPP-BOC, 7) and converted successfully to bacteriopurpurin-18-N-3′-(isothiocyanate)propylimide (13ChlPP-NCS, 9) as shown in Scheme 1. However, compared to model reactions, the overall yield of BChlPP-NCS from BChlPP dropped from 50% to 10% with BChlPP-BOC formation as the yield-limiting step. The conversion of BChlPP to its corresponding BChlPP-BOC, BChlPP-NH$_2$ and BChlPP-NCS was clearly demonstrated by their NMR spectra. As shown in FIG. 11, the 5.62 and the 3.31 ppm peaks observed in the BChlPP-BOC spectrum (shown partially) belonged to the N—H proton and the CH$_2$N protons adjacent to the BOC protection group, respectively. Cleavage of the BOC group led to the disappearance of the N—H peak and the upfield shift of the CH$_2$N resonance to 2.95 ppm. Further conversion of BChlPP—NH$_2$ to BChlPP—NCS shifts the above mentioned CH$_2$ resonance downfield to 3.85 ppm.

Scheme 2.
Synthesis of isothiocyanate-containing bacteriopurpurinimide, BChlPP-NCS (9) and the corresponding 2-deoxyglucose conjugate, BChlPP-2DG (10). Reaction conditions are the same as the model reaction shown in Scheme 1.

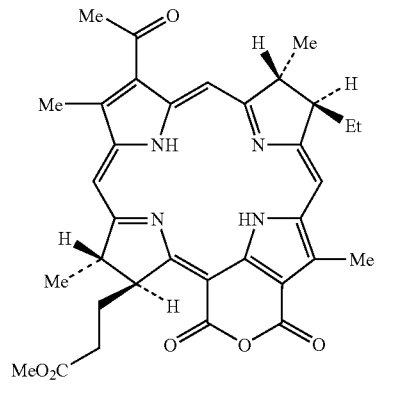

6

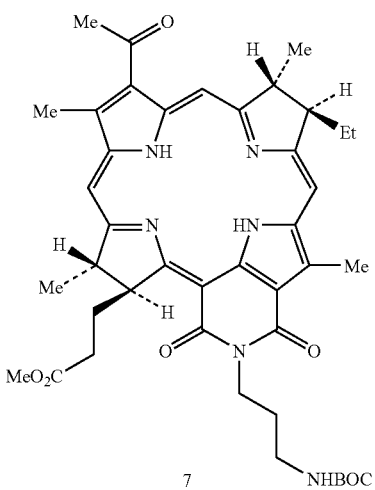

7

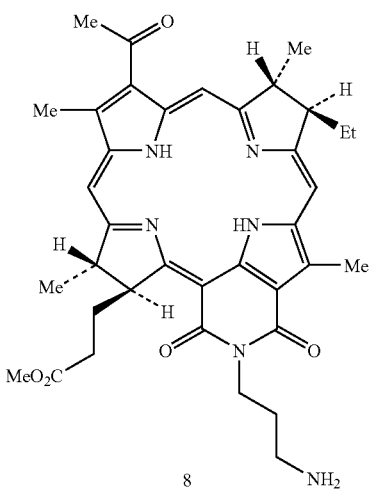

8

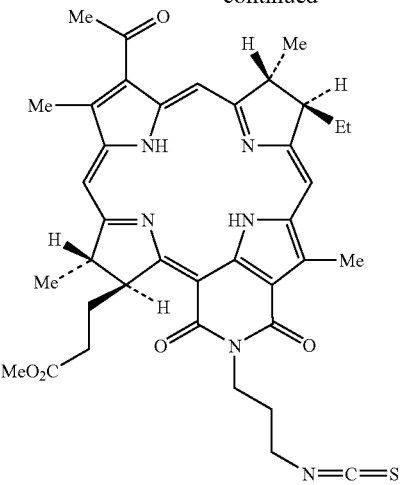

9

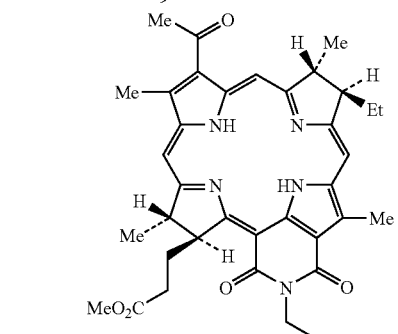

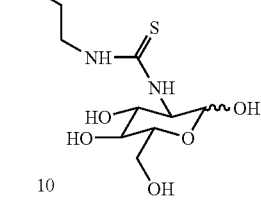

10

Figure 12A:
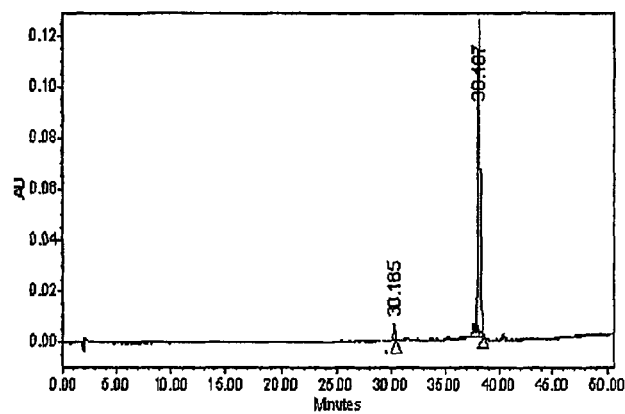
FIG. 12A. The HPLC chromatogram of BChlPP-2DG. RP-HPLC Column: ZARBOX-300SB_C8_4.6×250 mm; Solvent A: 0.1% TFA, B: $CH_3CN$; Gradient: From 10% B to 100% B for 45 min; Flow: 1 mL/min. At this condition, the retention time of BchlPP-2DG is 38.1 min. Purity of the compound: >90%.
Figure 12B:
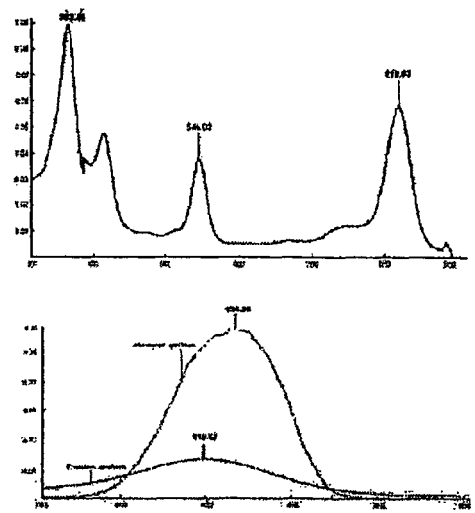
FIG. 12B. Absorption (top) and emission (bottom) spectra of BChlPP-2DG.

Next, a 2-deoxyglucose moiety was conjugated to BChlPP via the isothiocyanate coupling strategy to form the desired BChlPP-2DG, 10. Again, the coupling yield dropped significantly from 50% to 15% compared to the model reaction. These low yield steps are presumably caused by undesirable byproduct formation (e.g, the formation of 12-hydroxymethyl derivative of BChlPP-2DG) under basic conditions. Due to the limited amount of the final conjugate, a satisfactory NMR spectrum for compound 10 was not obtained. Nevertheless, the structure and the purity of BChlPP-2DG were confirmed by high resolution mass spectrometry and reverse phase HPLC (FIG. 12a), respectively. Based on the absorption and emission spectra of this conjugate (FIG. 12b), a preliminary study was performed to evaluate this agent in vivo in animal models; it proved to show great promise as a tumor-targeting NIR optical contrast agent (details described in a later section). However, due to the low yield, it is not practical to undertake-systematic evaluation of this new conjugate.

Figure 13A:
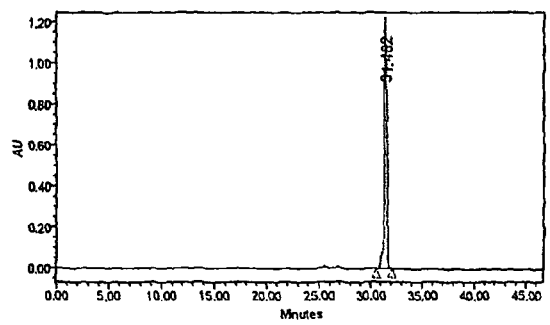
FIG. 13A. The HPLC chromatogram of BChlE6-2DG (retention time: 31.4 min, purity: 99%). BPLC method same as described in FIG. 12A.
Figure 13B:
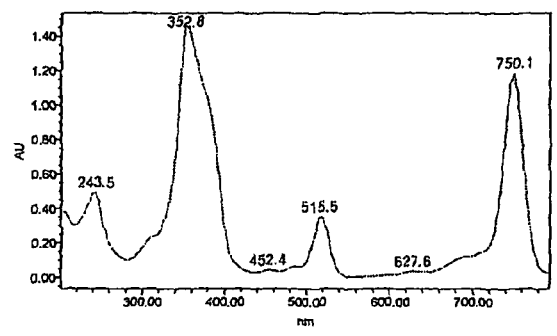
FIG. 13B. The absorption spectrum of the 31.4 min peak (BChlE6-2DG) obtained by HPLC. The maximum emission is 758 nm (spectrum not shown).

To improve the feasibility of using BChl-based bioconjugates for cancer detection and treatment, we explored another synthetic strategy to functionalize BChl. Bacteriopheophorbide a methyl ester 11 was first reacted with tert-butyl N-(-3-aminopropyl)-carbamate to form a single regioisomer, bacteriochlorin $e_6$-13-carboxy-N-3'-([30C-amino)propylamide, BChlE6-BOC (12). This intermediate was then converted to its corresponding amino- and isothiocyanate-containing BChl (BChlE6-NH₂ 13 and BChlE6-NCS 14) following the strategy described earlier. Compared with the previous procedure (10% overall yield from BChlPP to BChlPP-NCS, see Scheme 2), the new synthetic route from bacteriopheophorbide a methyl ester to BChlE6-NCS shown in Scheme 3 has the overall yield of 45%. Considering that bacteriopheophorbide a methyl ester is the precursor of BChlPP, the actual yield improved is five- to ten-folds. Furthermore, the yield of the final conjugation step to produce bacteriochlorin e6 2-deoxyglucosamide (BChlE6-2DG, 15) also increased from 15% to 60% compared to that of BChlPP-2DG. The structure of BChlE6-2DG was confirmed by ¹H, ¹³C NMR and high resolution mass spectrometry. The purity of BChlE6-2DG was 99% by RP-HPLC. FIG. 13 shows the IPLC chromatogram and the absorption spectra of the final conjugate.

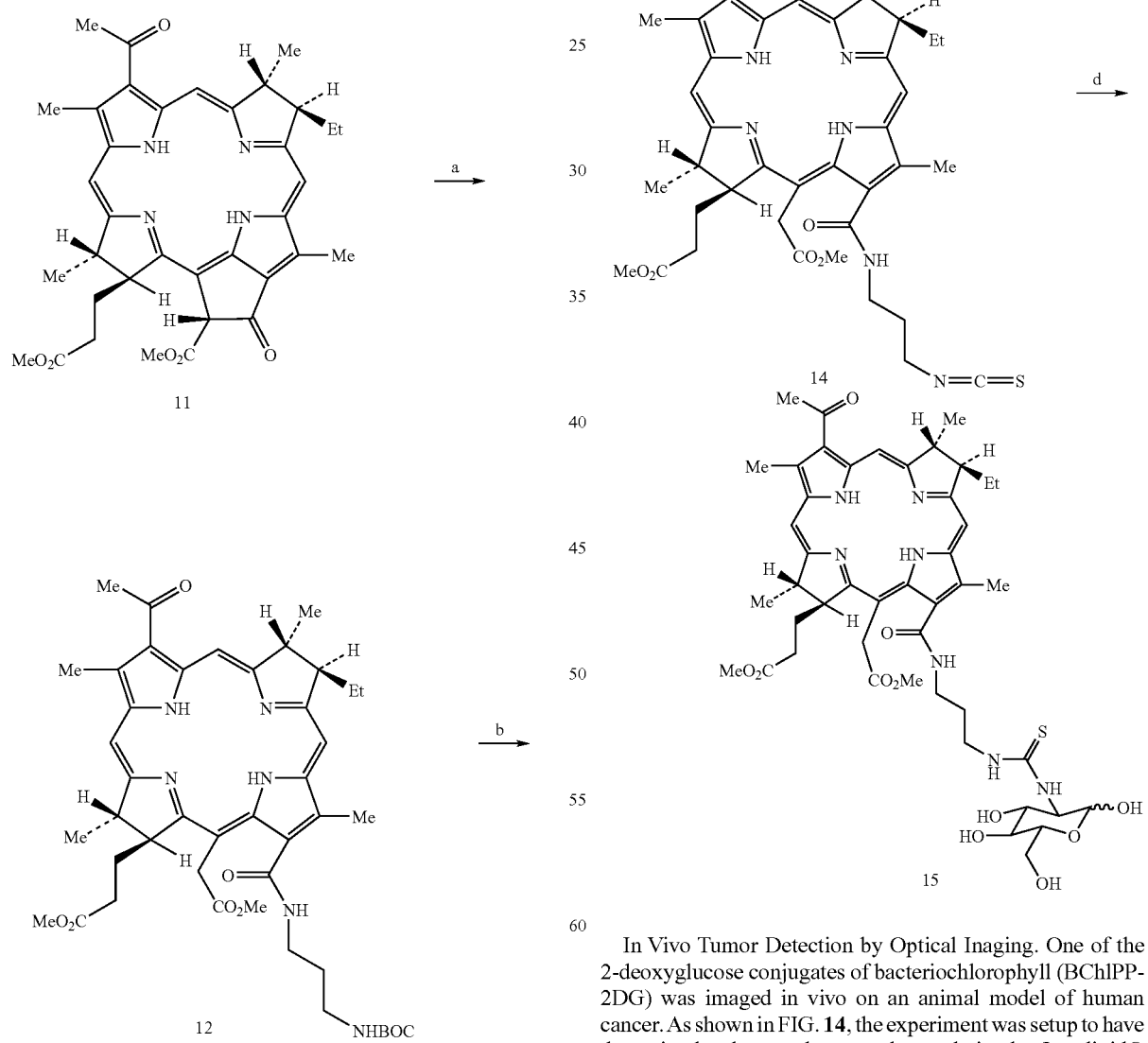

Scheme 3. Synthesis of BChlPP-NCS and its 2-deoxyglucose conjugate, BChlPP-2DG.

Figure 14:
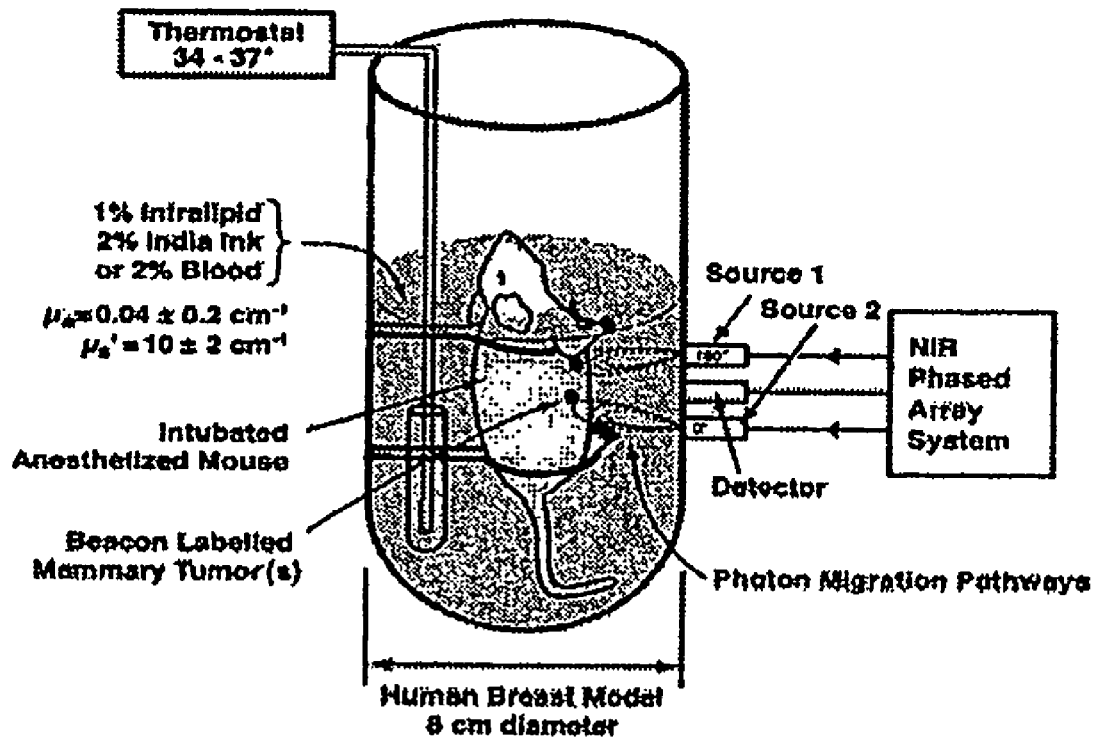
FIG. 14. Experimental set-up for in vivo animal tumor model imaging using the NIR phase array system.
Figure 15:
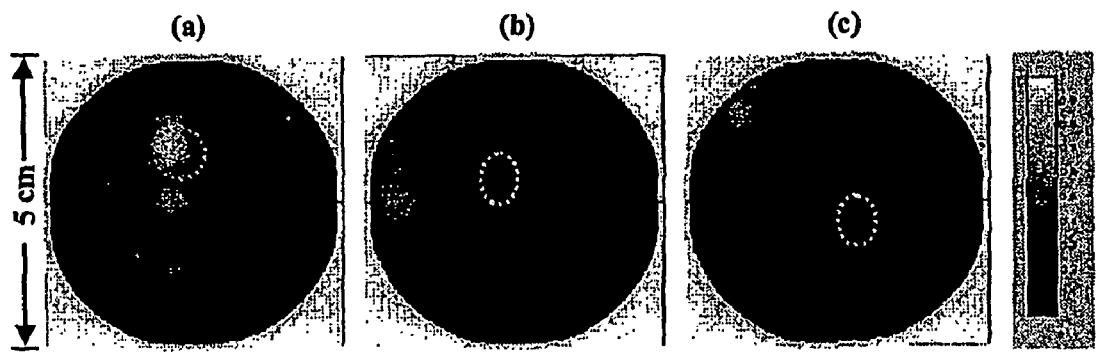
FIG. 15. Two-dimensional in vivo imaging of fluorescent contrast agents by the phased array system. (a) The localization of the 8 mm×8 mm submerged mouse tumor with tail vein injection of 200 μL 1 mg/nL BChlPP-2DG. (b) The localization of the 8 mm×4 mm submerged mouse tumor with tail vein injection of 200 μL 1 mg/mL ICG. (c) The localization of the 8 mm×6 mm submerged mouse tumor without injection of any contrast agent. In all cases, the tumors are 1.5 cm deep inside the media and the red dashed circle indicates the location and size of the tumor.

In Vivo Tumor Detection by Optical Inaging. One of the 2-deoxyglucose conjugates of bacteriochlorophyll (BChlPP-2DG) was imaged in vivo on an animal model of human cancer. As shown in FIG. 14, the experiment was setup to have the animal submerged up to the neck in the Intralipid® medium that simulates the scattering fatty tissues surrounding the tumor. The imaged animals are athymic nu/nu mice with implanted AR42J tumors (pancreatic acinar carcinoma) on the right thigh and injected with BChlPP-2DG after 12 hours of fasting. The imaging was performed on the anesthesized mice 3.5 hours after the injection of the contrast agent. Usually 200 µL of the contrast agents. The amount of injected contrast agents is usually 200 µL at a concentration of 1 mg/nL. The scattering media has similar optical properties as human breast tissue for studies of breast cancer models, and is maintained at physiological temperature (~37° C.). The tumor cells are hyper-metabolic compared with normal cells; consequently, they take up more glucose contrast agents into the tumor cells than nearby normal tissues. The mouse is kept alive throughout the experiment. The optical imaging probe is placed on the surface of the imaging chamber and scanned through a 5-cm-in-diameter area for subsurface localization of fluorescence enhanced tumor. FIG. 15a is the image obtained from BChl-2DG treated animals. The tumor region is enhanced. The localization of the tumor at a depth of 1.5 cm under the surface is accurately resolved, with a location error of 3.0±0.6 mm. For comparison, FIG. 15b shows the image of the mouse tumor following tail-vein injection of ICG. There is no significant enhancement in the tumor region, suggesting that the ICG could not provide high contrast between tumor and the normal tissue after 3.5 hours. This result is in agreement with the non-tumor-specificity of ICG and the depletion of ICG from the circulation system rapidly by the liver. (Achilefu, S.; Dorshow, R. B.; Bugaj, J. E.; Rajagopalan, R., Novel receptor-targeted fluorescent contrast agents for in vivo tumor imaging. *Investigative Radiology* 2000, 35, 479-485). FIG. 15c illustrates a negative control animal without the injection of the contrast agents; under these conditions the fluorescence phased array system does not detect the signals from the tumor.

CONCLUSION

The synthesis of two novel functionalized bacteriochlorophylls dyes is described. These new NIR dyes containing isothiocyanate functional groups are reactive toward primary amines; thus, they can be conjugated to biologically important compounds such as tumor-specific homing molecules. Compared with functionalized dyes derived from bacteriopurpurimides, dyes based on the bacteriochlorin $e_6$ moiety are produced in much better yield (5- to 10-fold), though the former has longer wavelength absorption and fluorescence emission (ex: 819 nm; em: 826 nm) than the latter (ex: 752 nm; em: 766 nm). Both of these functionalized bacteriochlorophylls showed successful conjugation to the glucose transporter-homing 2deoxyglucose moiety. BChlPP-2DG was further tested in vivo in animal tumors using a phase array NIR optical imaging system and showed promise as a the tumor-targeting agent for the detection and treatment of subsurface cancers.

What is claimed is:
1. A 2-deoxyglucose conjugate, wherein said conjugate is represented by the formula:

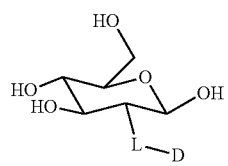

or a pharmaceutically acceptable salt thereof, wherein L is a linker group;

and D is selected from the group consisting of BChlPP of the formula

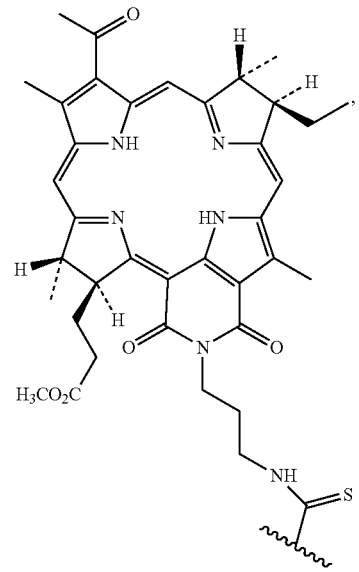

BChlE6 (bacteriochlorin $e_6$) of the formula

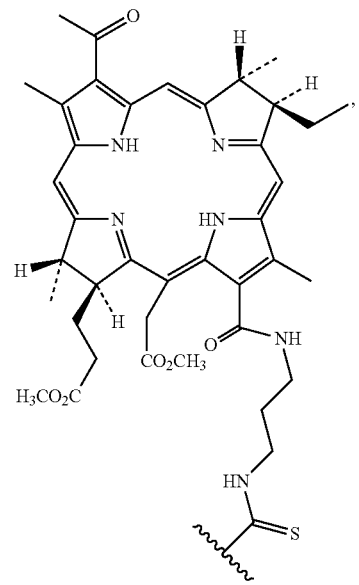

and NIR664(tricarbocyanine) of the formula

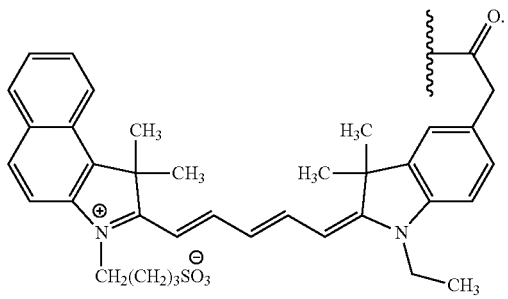

2. The conjugate of claim 1, wherein said linker group, L, is selected from the group consisting of a covalent bond, —NH—, -peptide-, -nucleic acid-, —O—, $(CH_2)_r$—O—, —NH—$CH_2$—$CH_2$—NH—, —NH—CH(COOH)—$CH_2$—NH—, —NH—$CH_2$—CH(COOH)—NH—, —NH—$CH_2$—$CH_2$—$CH_2$—NH, —O—$(CH_2)_r$NH—, S—$(CH_2)_r$—NH—, —S—$(CH_2)_r$—C(O)—, —NH—$CH_2$—C(O)—, —O—$CH_2$—$CH_2$—O—$CH_2$—$CH_2$—O, —NH—NH—C(O)—$CH_2$—, —NH—$C(CH_2)_2$—C(O)—, and —NH—NH—C(O)—$(CH_2)_r$—C(O)NH—N=., wherein r, in each instance, is from 2-5.

3. A pharmaceutical composition comprising the conjugate of claim 1 and a pharmaceutically acceptable carrier.

* * * * *